US012599731B2

(12) United States Patent
Botha et al.

(10) Patent No.: US 12,599,731 B2
(45) Date of Patent: Apr. 14, 2026

(54) SYSTEM AND METHOD FOR SENSING USAGE OF A CONTROLLED MEDICAL THERAPY DEVICE

(71) Applicant: 10xBeta, Brooklyn, NY (US)

(72) Inventors: Marcel Botha, Brooklyn, NY (US); Frederick Zacharias Kruger, Brooklyn, NY (US); Johannes Michiel Bredenkamp, Brooklyn, NY (US)

(73) Assignee: 10XBeta, Brooklyn, NY (US)

( * ) Notice: Subject to any disclaimer, the term of this patent is extended or adjusted under 35 U.S.C. 154(b) by 1238 days.

(21) Appl. No.: 17/313,066

(22) Filed: May 6, 2021

(65) Prior Publication Data

US 2021/0268217 A1 Sep. 2, 2021

Related U.S. Application Data

(63) Continuation-in-part of application No. 17/166,300, filed on Feb. 3, 2021.

(Continued)

(51) Int. Cl.
*A61M 15/08* (2006.01)
*A61M 11/00* (2006.01)
*A61M 15/00* (2006.01)

(52) U.S. Cl.
CPC .......... *A61M 15/08* (2013.01); *A61M 11/006* (2014.02); *A61M 15/0086* (2013.01);
(Continued)

(58) Field of Classification Search
CPC .............. A61M 15/08; A61M 15/0086; A61M 15/0083; A61M 15/0081; A61M 11/007;
(Continued)

(56) References Cited

U.S. PATENT DOCUMENTS 5,284,133 A * 2/1994 Burns ............... A61M 15/0066
128/203.14
6,330,976 B1 * 12/2001 Dymetman ........ H04N 1/32042
235/487

(Continued)

FOREIGN PATENT DOCUMENTS

CN 103582505 A 2/2014
CN 104284733 A 1/2015
(Continued)

OTHER PUBLICATIONS

Office Action issued Mar. 5, 2024 in connection with Russian Patent Application No. 2022123537.

(Continued)

*Primary Examiner* — Scott J Medway
*Assistant Examiner* — Lei Nmn Gonzalez
(74) *Attorney, Agent, or Firm* — TROUTMAN PEPPER LOCKE LLP

(57) ABSTRACT

A nasal spray device can include housing having a sensor and a nozzle having a housing interface with a graphical image thereon. The sensor can be configured to sense movement of the graphical image when the nozzle moves relative to the housing, for instance during administration of medicine from the nasal spray device. The sensor can include an infrared proximity sensor that senses infrared reflectivity from the graphical image. The infrared proximity sensor can also be used to measure distance to a surface of a vial within the housing to thereby detect insertion of the vial into the housing.

19 Claims, 25 Drawing Sheets

Related U.S. Application Data

(60) Provisional application No. 62/969,421, filed on Feb. 3, 2020.

(52) U.S. Cl.
CPC ............... *A61M 2205/3327* (2013.01); *A61M 2205/583* (2013.01); *A61M 2205/587* (2013.01); *A61M 2205/702* (2013.01)

(58) Field of Classification Search
CPC ............ A61M 11/006; A61M 2230/63; A61M 2230/06; A61M 2209/00; A61M 2205/8243; A61M 2205/8206; A61M 2205/7527; A61M 2205/702; A61M 2205/609; A61M 2205/587; A61M 2205/584; A61M 2205/583; A61M 2205/581; A61M 2205/52; A61M 2205/505; A61M 2205/3606; A61M 2205/3592; A61M 2205/3584; A61M 2205/3553; A61M 2205/3386; A61M 2205/3327; A61M 2205/3317; A61M 2205/3306; A61M 2205/276; A61M 2205/18; A61M 2205/14; A61M 2205/103; A61M 2202/0468; A61M 15/0001; A61M 2202/0007; A61M 2210/0618; A61M 2205/3576; A61B 5/4833; A61B 5/1172; A61B 5/02438; B05B 11/1059; B05B 11/0054; B05B 11/0038; B05B 12/02; G06F 21/32; G06F 21/36; G06V 40/1318; G06V 40/10; H04W 12/06; H04L 63/0861; G16H 20/13; A61P 25/24
See application file for complete search history.

(56) References Cited

U.S. PATENT DOCUMENTS

| | | | | |
|---|---|---|---|---|
| 6,471,637 | B1 * | 10/2002 | Green | A61B 1/00045 600/137 |
| 7,077,286 | B2 | 7/2006 | Shows et al. | |
| 7,100,839 | B2 * | 9/2006 | Farina | A61M 15/00 700/282 |
| 8,794,547 | B2 | 8/2014 | Zumberger et al. | |
| 8,869,791 | B2 | 10/2014 | Sauzade et al. | |
| 8,950,393 | B2 | 2/2015 | Holakovsky et al. | |
| 9,364,620 | B2 | 6/2016 | Carter | |
| 10,706,239 | B1 * | 7/2020 | Tran | G06K 1/121 |
| 10,862,350 | B2 * | 12/2020 | Keeley | H02J 50/80 |
| 11,017,214 | B1 * | 5/2021 | Trani | G06V 40/166 |
| 12,023,709 | B2 | 7/2024 | Bons et al. | |
| 2003/0000524 | A1 | 1/2003 | Anderson et al. | |
| 2005/0067494 | A1 * | 3/2005 | Ito | G06K 7/10702 235/462.24 |
| 2005/0150488 | A1 | 7/2005 | Dave | |
| 2005/0183718 | A1 | 8/2005 | Wuttke et al. | |
| 2007/0041622 | A1 * | 2/2007 | Salva Calcagno | G06V 40/1359 382/124 |
| 2008/0029544 | A1 | 2/2008 | Margheritis et al. | |
| 2008/0173067 | A1 * | 7/2008 | Farina | B05B 11/10 73/1.16 |
| 2009/0139724 | A1 | 6/2009 | Gray et al. | |
| 2009/0194104 | A1 | 8/2009 | Van Sickle | |
| 2009/0301481 | A1 | 12/2009 | Sullivan | |
| 2010/0084433 | A1 | 4/2010 | Cater et al. | |
| 2010/0277696 | A1 * | 11/2010 | Huebner | G03B 21/00 353/30 |
| 2011/0095104 | A1 | 4/2011 | Swan | |
| 2012/0296291 | A1 | 11/2012 | Painchaud et al. | |
| 2013/0008436 | A1 | 1/2013 | Von Hollen et al. | |
| 2014/0081216 | A1 | 3/2014 | Eberhart et al. | |
| 2015/0151041 | A1 | 6/2015 | Yodfat | |
| 2017/0007783 | A1 * | 1/2017 | Helmlinger | A61M 15/008 |
| 2017/0072144 | A1 | 3/2017 | Van Sickle et al. | |
| 2018/0059125 | A1 * | 3/2018 | Gorin | G01N 1/38 |
| 2018/0060527 | A1 | 3/2018 | Kalyanpur et al. | |
| 2019/0019306 | A1 * | 1/2019 | Umanskiy | G06T 7/80 |
| 2019/0368983 | A1 * | 12/2019 | Einsle | B01L 1/025 |
| 2020/0383875 | A1 | 12/2020 | Banov et al. | |
| 2020/0394002 | A1 | 12/2020 | Blanco Gabella | |
| 2021/0169355 | A1 * | 6/2021 | Patel | A61B 5/0004 |
| 2022/0088327 | A1 | 3/2022 | Fuller et al. | |
| 2022/0240771 | A1 * | 8/2022 | Domecus | A61B 1/00045 |
| 2022/0379046 | A1 | 12/2022 | Decock et al. | |
| 2023/0016850 | A1 * | 1/2023 | Tweedie | A61M 15/0091 |

FOREIGN PATENT DOCUMENTS

| | | | | | |
|---|---|---|---|---|---|
| DE | 102004009435 | A1 * | 12/2005 | ........ | A61M 15/0083 |
| EP | 2730340 | B1 | 10/2018 | | |
| JP | 2019-530549 | A | 10/2019 | | |
| RU | 2607188 | | 1/2017 | | |
| RU | 2648446 | | 3/2018 | | |
| TW | 202131960 | A * | 9/2021 | ........ | A61M 15/0025 |
| WO | 1987/05813 | A1 | 10/1987 | | |
| WO | 01/93932 | A1 | 12/2001 | | |
| WO | 2002/100468 | A2 | 12/2002 | | |
| WO | 2005/009325 | A2 | 2/2005 | | |
| WO | 2006/003343 | A1 | 1/2006 | | |
| WO | 2009086009 | A1 | 7/2009 | | |
| WO | 2011/051602 | A1 | 5/2011 | | |
| WO | 2015/139874 | A1 | 9/2015 | | |
| WO | 2016/100564 | A1 | 6/2016 | | |
| WO | 2018-039562 | A1 | 3/2018 | | |
| WO | 2020/023547 | A1 | 1/2020 | | |

OTHER PUBLICATIONS

Extended European Search Report issued Dec. 3, 2024 in European Application No. 21939950.8.
Extended European Search Report issued Mar. 21, 2025 in European Application No. 24222923.5.
Office Action dated Sep. 2, 2025, issued in counterpart JP Patent Application No. 2025-051201 (with English translation).
Office Action dated May 31, 2025 issued in Chinese Application No. 202180026436.6 (including English translation).
Written Opinion and Search Report issued in International Application No. PCT/US2021/031014 dated Oct. 14, 2021.
Office Action issued in U.S. Appl. No. 17/166,300 dated May 20, 2025.
International Preliminary Report on Patentability mailed Jul. 28, 2022, issued in International Application No. PCT/US2021/016304.
International Search Report mailed Jun. 8, 2021, issued in International Application No. PCT/US2021/016304.
Written Opinion of the International Search Authority mailed Jun. 8, 2021, issued in International Application No. PCT/US2021/016304.
Office Action issued Nov. 29, 2024 in connection with U.S. Appl. No. 17/166,300.
Extended European Search Report issued Jan. 17, 2024 in connection with European Application No. 21750326.7.

\* cited by examiner

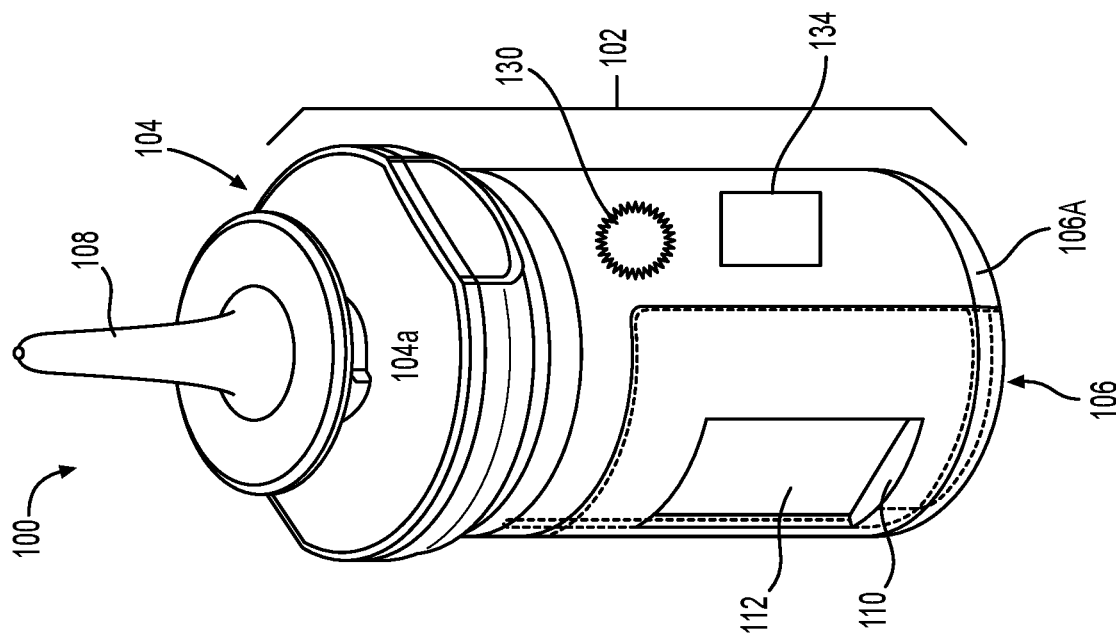
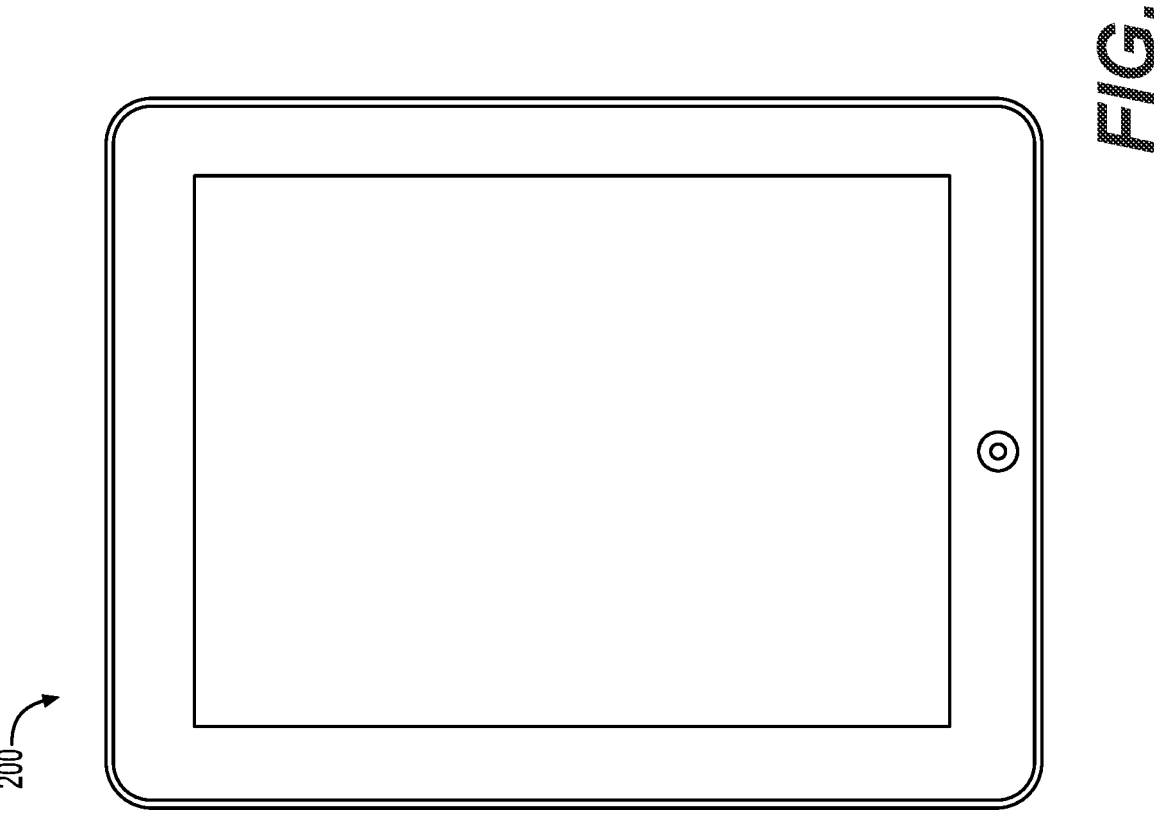
*FIG. 1*

FIG. 18A          FIG. 18B

SYSTEM AND METHOD FOR SENSING USAGE OF A CONTROLLED MEDICAL THERAPY DEVICE

CROSS-REFERENCE TO RELATED APPLICATIONS

This application is a continuation in part of U.S. patent application Ser. No. 17/166,300 filed on Feb. 3, 2021 which claims priority to U.S. Provisional Patent Application No. 62/969,421 filed on Feb. 3, 2020, the disclosures of each of which are incorporated herein by reference in their entireties.

BACKGROUND OF THE INVENTION

1. Field of the Invention

The present invention relates to a system and method for controlling the dispensing of medication, and, more specifically, to a system and method for dispensing medication through a time-controlled device linked to a web platform.

2. Description of the Related Art

Conventional personal medication dispensing devices, such as intranasal spray devices, are often effectively used to deliver atomized medications. Traditional intranasal spray devices consist of a pump with an elongated nozzle which atomizes liquid as the liquid is propelled through the nozzle and out the delivery orifice. The resulting mist is inhaled and efficiently absorbed through the tissue, thereby providing an effective treatment.

Intranasal spray devices have been utilized to provide medication for conditions ranging from allergies, pain relief and depression. For conditions such as pain relief and depression, the risk of abuse associated with the medications provided within the device is high due to the addictive nature of medication treating those conditions. Ketamine, for example, has shown great effectiveness in treating serious conditions such as bipolar depression. However, given the addictive nature of medications such as ketamine, healthcare providers are hesitant to administer or otherwise prescribe them for home use. Healthcare providers are often concerned with patients abusing or misusing the medication, a person other than the patient abusing the medication, and theft and/or sale of the medication.

Abuse and misuse is not only attributed to the addictive nature of the medications but also the efficacy of the medication at delivering relief for the patient's condition. Patients may be driven to use more than their prescribed dosage due to the relief the medication provides. Consequently, patients in need of such medications may only receive a small dosage or supply per visit to a healthcare provider. As a result, some patients must visit their healthcare provider frequently, such as multiple times per week. Numerous required visits to a healthcare provider are not only inconvenient but can also act as a barrier to access to medication for those who cannot afford burdensome transportation or take extended time away from their place of employment.

BRIEF SUMMARY OF THE INVENTION

Systems and methods are provided for dispensing medication with a locking dispensing device. The dispensing device can be shaped to form an exoskeleton around a medicinal vial. The dispensing device can include one or more locking mechanisms to prevent removal of the vial and/or administration of dosages. The system can include the dispensing device and a computing device that can be linked to the dispensing device to configure the dispensing devices' parameters (e.g. timeout, tampering detection, improper usage, biometric input, user authentication) for engaging and/disengaging the locking mechanisms.

The dispensing device can include a nozzle and a housing that can be integral or separable components that can be slidably engaged to each other to form an exoskeleton around the vial. The nozzle can include a housing interface configured to slidably engage the nozzle to the housing.

The dispensing device can include a vial lock that can be locked to prevent removal of the vial from the dispensing device and unlocked to allow removal of the dispensing device. In some examples, the vial lock can further include stops to limit movement of the nozzle in relation to the housing (e.g. set a completely extended position of the nozzle and/or completely depressed position of the nozzle). In examples where the nozzle is separable from the housing, the vial lock can further inhibit separation of the nozzle from the housing when locked and allow separation of the nozzle from the housing when unlocked.

The dispensing device can include a dose lock that can be locked to prevent movement of the nozzle in relation to the housing, thereby preventing administration of medication. The dose lock can be unlocked to allow the nozzle to be depressed into and/or extend out of the housing, thereby allowing administration of medication. In examples where the nozzle is separable from the housing, the dose lock, when locked, can further inhibit separation of the nozzle from the housing, and/or removal of the vial from the device.

The dispensing device can include sensors configured to detect partial depression of the nozzle and electrical circuitry configured to lock the dose lock in response to signals from the sensors. The sensors can include optical sensors positioned to view movement of the nozzle in relation to the housing.

In examples where the nozzle is separable from the housing, the nozzle can function together with a vial, absent the housing, to deliver medication. The housing can include the dose lock and the vial lock. The nozzle can include features to which the dose lock and/or vial lock can engage and lock. The housing can include sensors for detecting movement of the nozzle. The nozzle can include features thereon that are detectable by the sensors of the housing. The sensors and features on the nozzle can be positioned and otherwise configured to allow the device to detect partial depression of the nozzle.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a perspective view of an embodiment of the system according to the present invention;

DETAILED DESCRIPTION OF THE INVENTION

Figure 2:
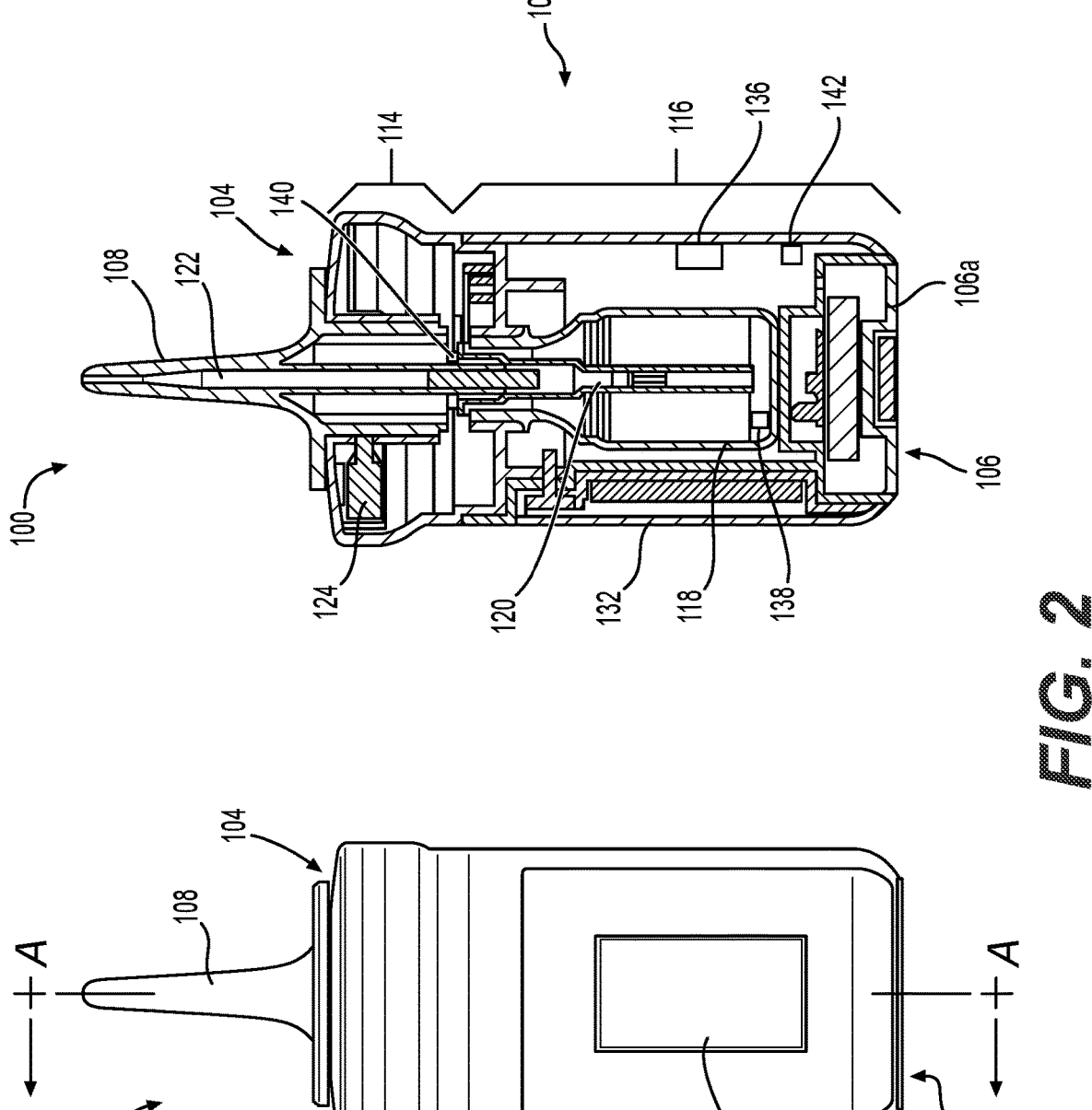
FIG. 2 is a schematic cross-sectional representation of an embodiment of the system in an unlocked position, taken along line A.

Referring to the Figures, the present invention may be a system, a method, and/or a computer program product. The computer program product may include a non-transitory computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Referring again to the drawings, wherein like reference numerals refer to like parts throughout, there is seen in FIG. 1 a perspective view of an embodiment of the system according to the present invention. FIG. 1 shows an embodiment of the system comprising a dispensing device 100 and a computing device 200. The computing device 200 may be a smartphone, portable tablet, laptop computer, desktop computer, and any other like devices. FIG. 1 also shows the exterior components of an embodiment of the dispensing device 100. The dispensing device 100 comprises a cylindrical housing 102 having a first closed end 104 and a second closed end 106. A nozzle 108 extends perpendicular from a surface 104a of the first closed end 104. The second closed end 106 may further comprise a baseplate 106a secured to the housing 102 with fasteners such as star screws, which will prevent easy tampering with the housing 102. Other fasteners are contemplated such as magnetic fasteners, custom "keyed" screws, or similar locking devices. The housing 102 further comprises a recess 110 with a display screen 112 therein. The display screen may be a panel display, such as a monochrome OLED graphic display, or other LED displays, for example.

Referring to FIG. 2, there is shown a schematic cross-sectional representation of an embodiment of the system in an unlocked position, taken along line A. FIG. 2 shows the interior components of the dispensing device 100 in an unlocked position wherein the nozzle 108 is depressed. The housing 102 of the dispensing device 100 further comprises a first portion 114 and a second portion 116. The first portion 114 of the housing 102 is connected to both the first closed end 104 and the second portion 116.

In the depicted embodiment, the second portion 116 of the housing 102 is connected to the second closed end 106 or the baseplate 106a and provides a base for the dispensing device 100. The second portion 116 houses the liquid container 118, which is configured to store liquid medicinal compositions. In the depicted embodiment, the liquid container 118 is cylindrical such to provide an efficient fit within the similarly cylindrical housing 102. An example of a cylindrical liquid container 118 is a thread size stock vial.

In order to provide access to the medicinal contents of the liquid container 118, the liquid container 118 comprises a pump assembly 120. In the embodiment shown in FIG. 2, the pump 120 is centrally located within the liquid container 118. The pump assembly 120 is structured and operates substantially as standard pump assemblies used in conventional intranasal spray devices. As pressure is applied on the nozzle 108 towards the surface 104a of the first closed end 104, the pump assembly 120 propels the liquid medical composition stored within the liquid container 118 through a channel 122 in the nozzle 108, expelling the liquid medical composition from the dispensing device 100. Thus, in an unlocked position, the liquid medical composition can be freely expelled from the dispensing device 100.

Figure 3A:
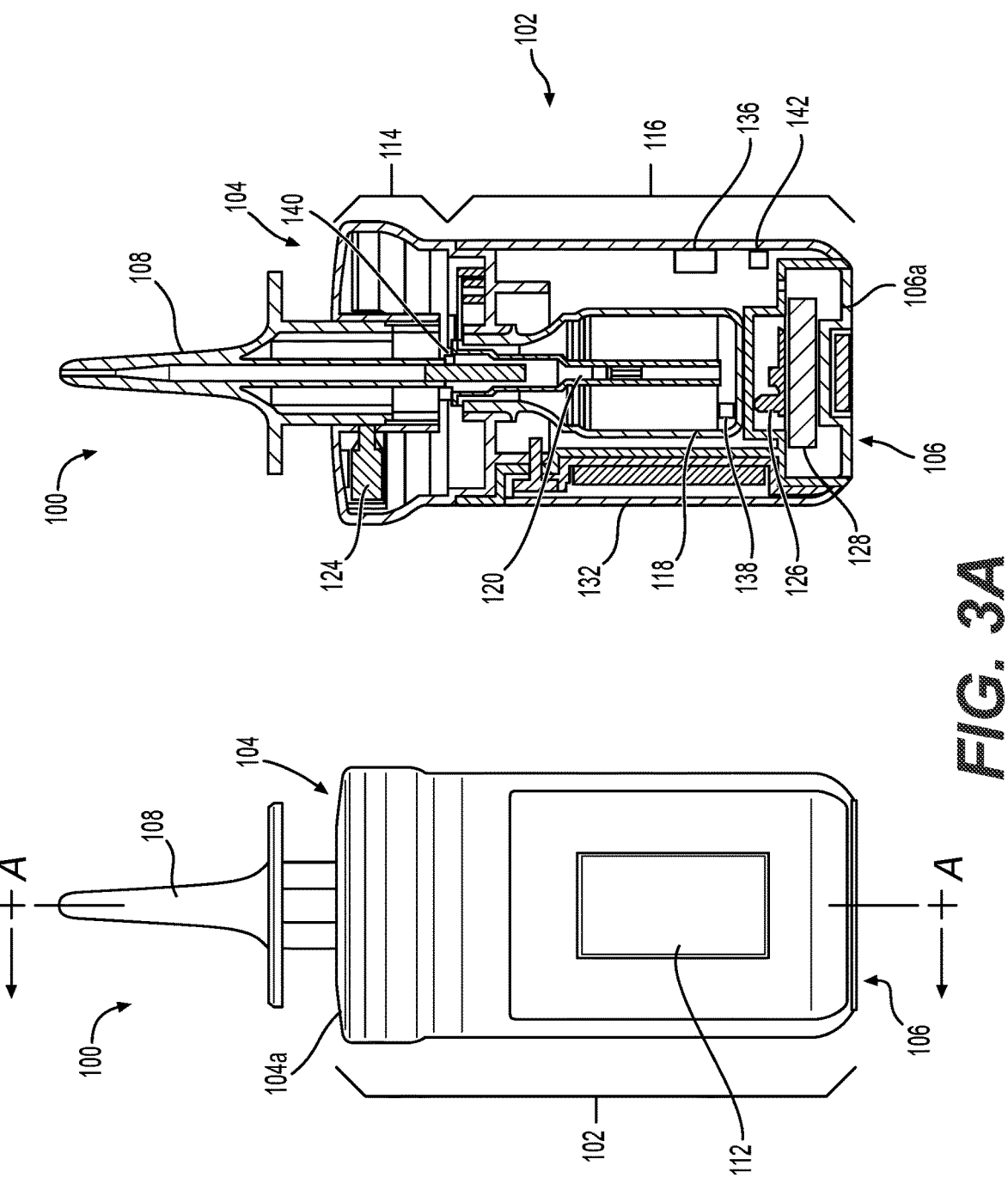
FIG. 3A is a schematic cross-sectional representation of an embodiment of the system in a locked position, taken along line A.
Figure 3B:
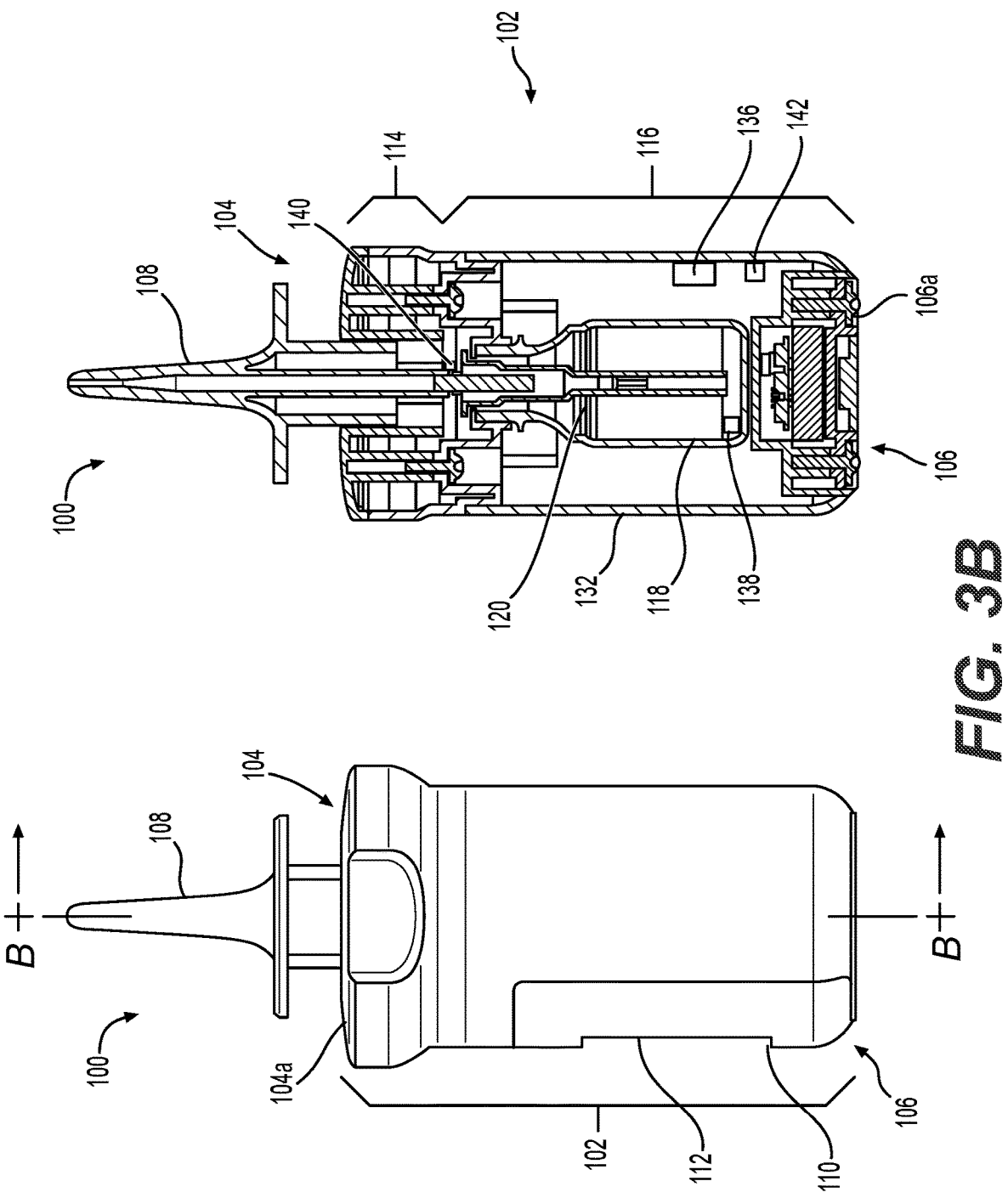
FIG. 3B is a schematic cross-sectional representation of an embodiment of the system in a locked position, taken along line B.

Referring to FIGS. 3A-3B, there are shown schematic cross-sectional representations of an embodiment of the system in a locked position, taken along lines A and B, respectively. In the depicted embodiment, the first portion 114 of the housing 102 further comprises a solenoid 124 locking mechanism therein. The solenoid 124 operates perpendicular to the motion of the pump assembly 120. In one embodiment, when the solenoid 124 is activated, it moves into the path of the nozzle 108 thereby blocking full movement of the nozzle 108 towards the surface 104a of the first closed end 104 and preventing the pump assembly 120 from expelling the liquid medicinal composition from the dispensing device 100. The solenoid 124 is shown in an unlocked position in FIG. 2 and a locked position in FIGS. 3A-3B. In alternative embodiments, the solenoid 124 may comprise attachments such as a U-clip which blocks the path of the nozzle 108 and interrupts the motion of the pump assembly 120.

Referring still to FIGS. 3A-3B, in the depicted embodiment, the solenoid 124 is activated in response to an electrical signal sent from a processor, such as a printed circuit board 126. As shown in FIGS. 3A-B, the printed circuit board 126 is located within the second portion 116 of the housing 102 towards the second closed end 106. The printed circuit board 126 is operably connected to and powered by a battery 128 also located within the second portion 116 at the second closed end 106. The battery 128 can be a rechargeable lithium ion battery or a similar type power source.

Figure 7A:
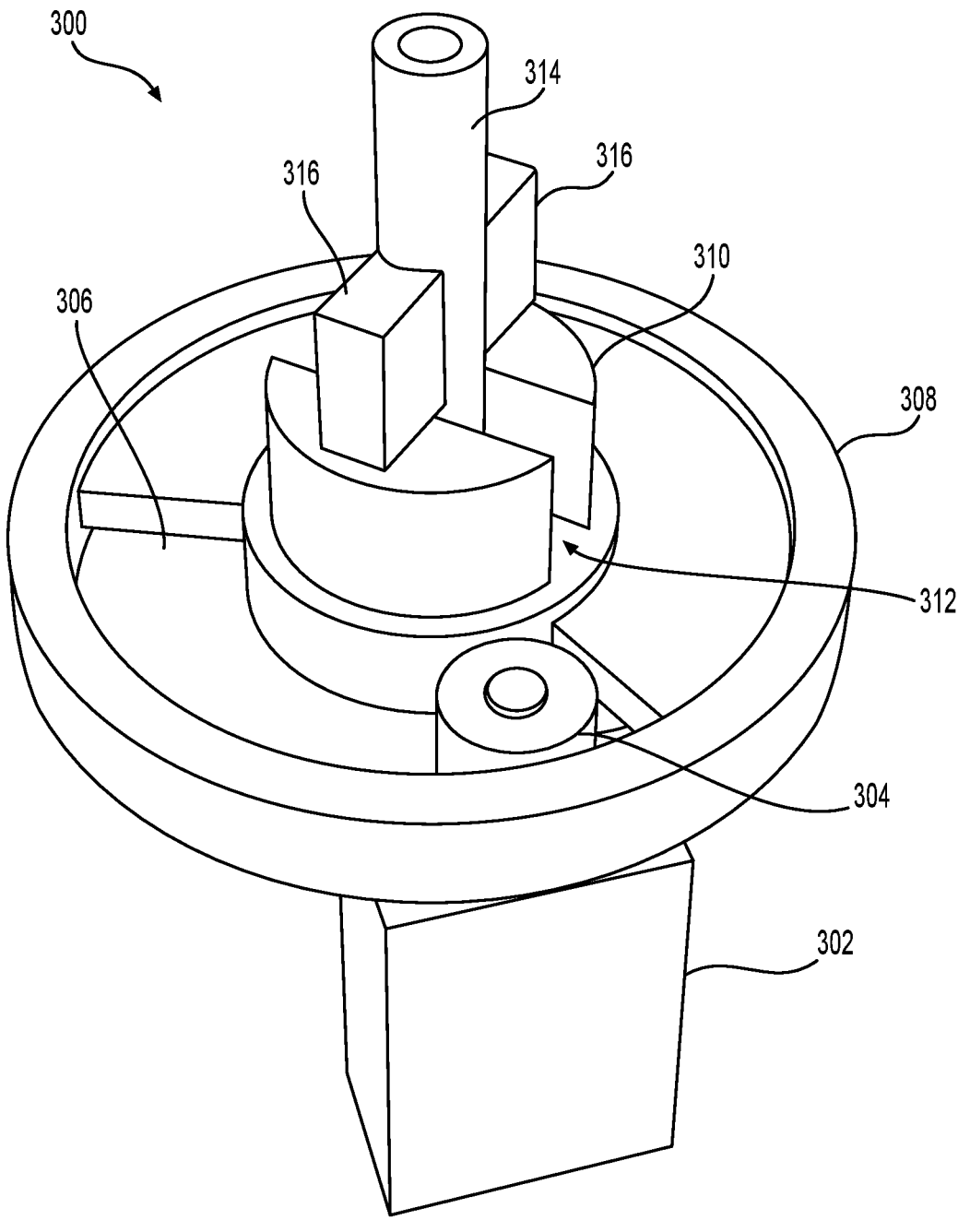
FIG. 7A is a top perspective view of an embodiment of the motor assembly in the locked position.

In an alternative embodiment, the locking mechanism is a motor assembly 300. In FIGS. 7A-8C, there are shown various views of an embodiment of the motor assembly 300 locking mechanism. Referring first to FIG. 7A, a top perspective view of the motor assembly 300 is shown in the locked position. The motor assembly 300 comprises a motor 302 connected to a first gear 304, which is positioned within an opening 306 of an internal gear wheel 308. The internal gear wheel 308 comprises a central lock 310 with a keyway 312 extending therethrough. Similar to the embodiment wherein the locking mechanism is a solenoid 124 (FIGS. 3A-3B), the motor assembly 300 interrupts or otherwise blocks the motion of the pump assembly 120. In the embodiment shown in FIG. 7A, the shaft 314 of a pump assembly 120 extends through the central lock 310 of the internal gear wheel 308. To facilitate locking, there are one or more keys 316 protruding from the shaft 314 of the pump assembly 120. The keys 316 are configured or otherwise fitted to slide into the keyway 312 of the central lock 310. In the embodiment shown in FIG. 7A, the keys 316 rest on the central lock 310 and are blocked from sliding into the keyway 312. Therefore, a nozzle 108 attached to the pump assembly 120 is not compressible when the keys 316 are not in alignment with the keyway 312.

Figure 7B:
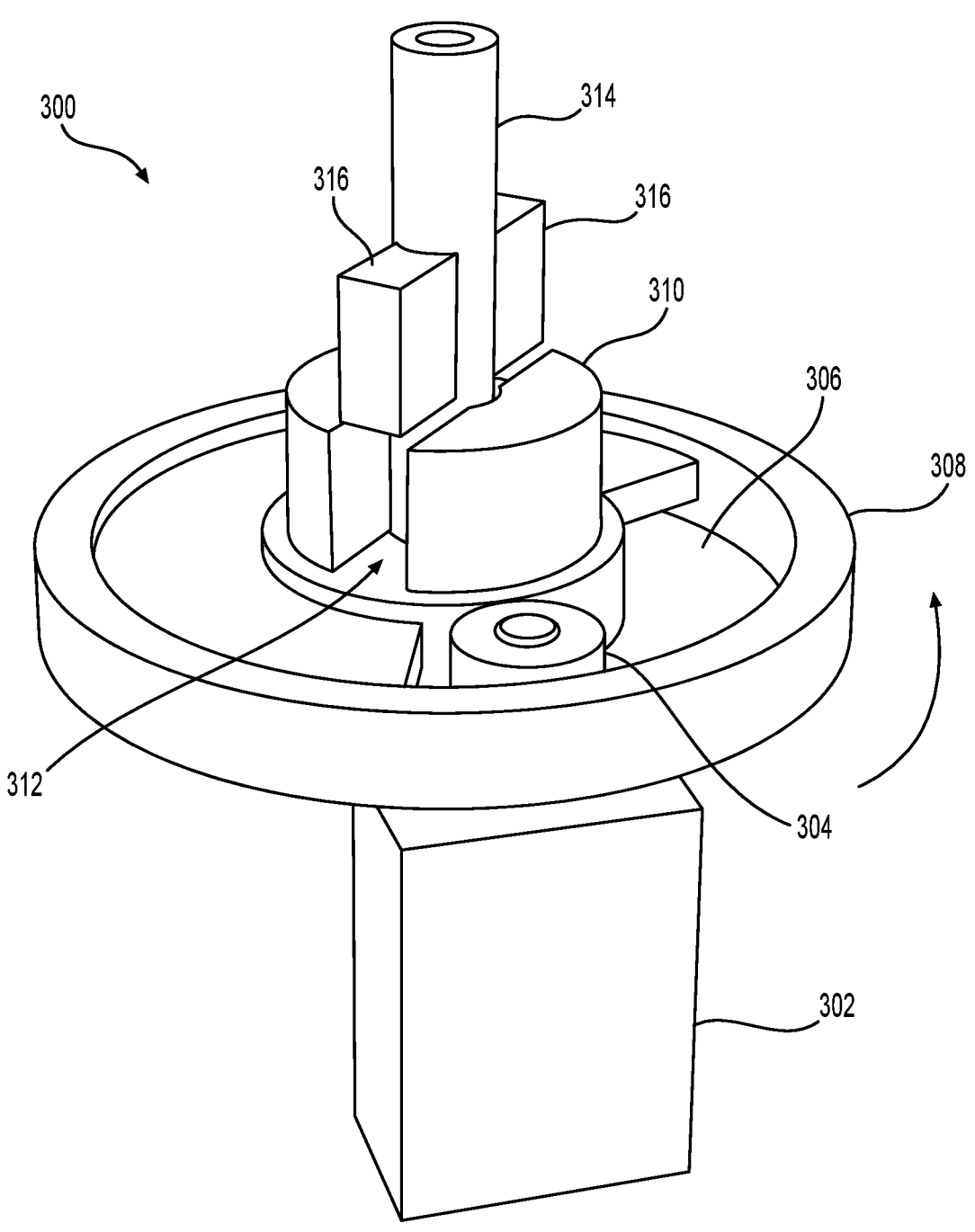
FIG. 7B is a side perspective view of an embodiment of the motor assembly in the unlocked position.
Figure 7C:
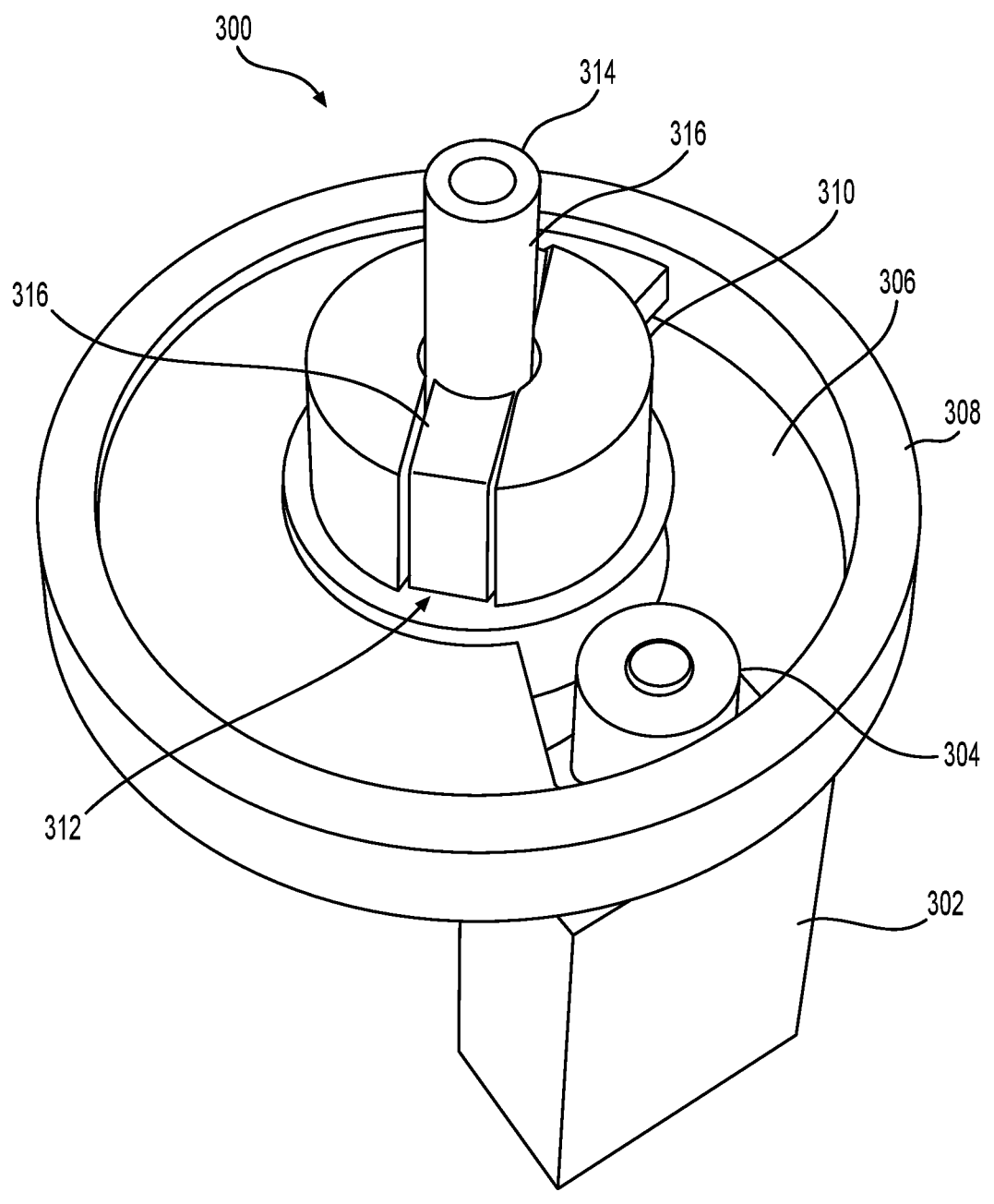
FIG. 7C is a top view of an embodiment of the motor assembly in the unlocked position.

Referring now to FIGS. 7B-7C, there is shown a side perspective view and a top view of the motor assembly 300 in the unlocked position. From the locked position, shown in FIG. 7B, the motor 302 is activated by an electrical signal from the printed circuit board 126, which rotates the gear 304 thereby rotating the internal gear wheel 308. The opening 306 in the internal gear wheel 308 limits rotation of the internal gear wheel 308 as it may only rotate in either direction until it catches on the gear 304. As the internal gear wheel 308 rotates, the lock 310 and keyway 312 rotate as well. The internal gear wheel 308 rotates until it is in the unlocked position, shown in FIG. 7B. In the unlocked position, the keys 316 of the shaft 314 of the pump assembly 120 are aligned with the keyway 312, which extends through the lock 310. Once the motor assembly 300 is in the unlocked position, the nozzle 108 can be compressed. Compression of the nozzle 108 causes the keys 316 on the shaft 314 of the pump assembly 120 to slide into the keyway 312 of the lock 310, as shown in FIG. 7C. When the nozzle 108 is released, the keys 316 on the shaft 314 slide out from the keyway 312 and the internal gear wheel 308 may be rotated back to the locked position shown in FIG. 7A Turning now to FIGS. 8A-8C, there are shown various perspective views of the first portion 114 and second portion 116 of an embodiment of the housing 102 with a motor assembly 300. In the depicted embodiment, the first portion 114 of the housing 102 contains the pump assembly 120, the printed circuit board 126, and the battery 128 (not shown), and the second portion 116 of the housing 102 contains the liquid container 118 (not shown). Referring first to FIG. 8B, there is a side view of the first portion 114 of the housing 102 and the second portion 116 of the housing 102 in an unlocked position. The first portion 114 of the housing 102 has apertures 318 along the outer circumference of its bottom surface 320. A disc 324 stacked on top of the bottom surface 320 of the first portion 114 of the housing 102 has cutouts 326 along the outer circumference of the disc 324. The cutouts 326 which are configured to align with the apertures 318 in the bottom surface 320 of the first portion 114. Still referring to FIG. 8B, the motor 302 of the motor assembly 300 comprises a second gear 322 on a side of the motor 302 opposite the first gear 304. The second gear 322 is used to rotate the disc 324 on the bottom surface 320 of the first portion 114.

Figure 8A:
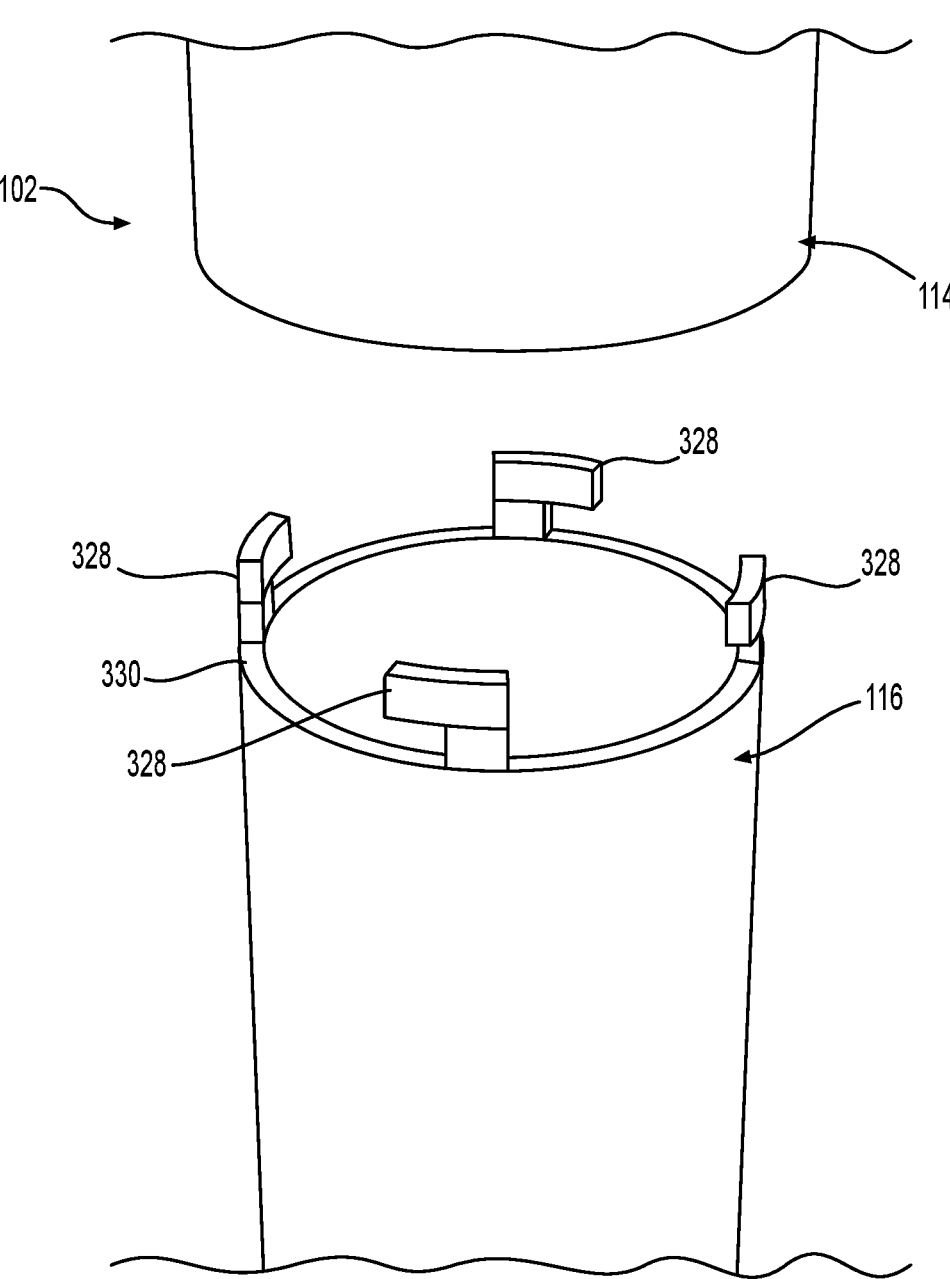
FIG. 8A is a side perspective view of an embodiment of the first and second portions of the housing having a motor assembly.
Figure 8B:
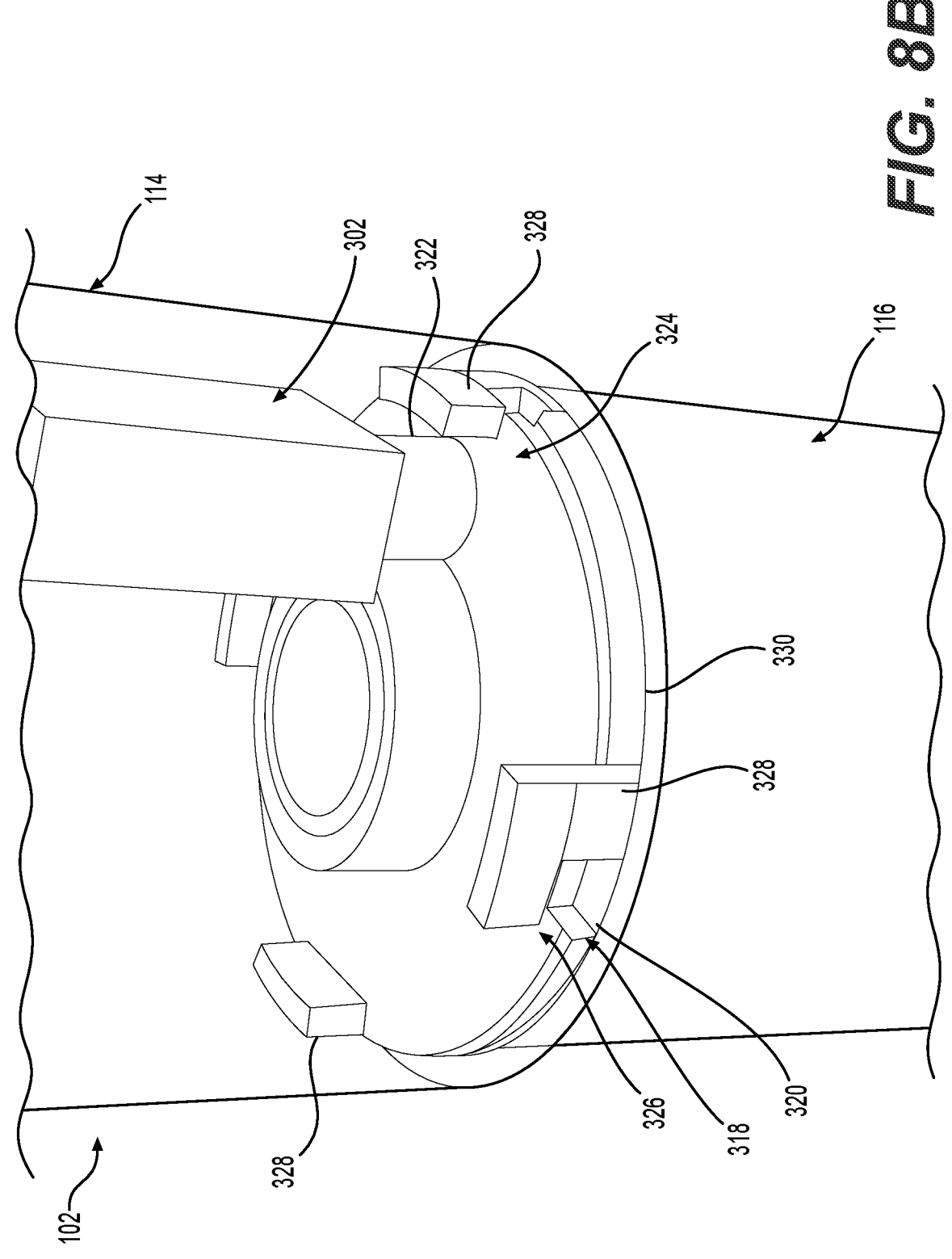
FIG. 8B is another side perspective view of an embodiment of the first and second portions of the housing in an unlocked position.

Referring now to FIG. 8A, the second portion 116 of the housing 102 comprises a plurality of L-shaped flanges 328 extending from the top surface 330 of the second portion 116. The L-shaped flanges 328 are configured to fit through the apertures 318 in the bottom surface 320 of the first portion 114 and the cutouts 326 in the disc 324. In the unlocked position, shown in FIG. 8B, the L-shaped flanges 328 are aligned with the apertures 318 in the bottom surface 320 of the first portion 114 and the cutouts 326 in the disc 324. Therefore, the second portion 116 can be pulled and removed from the first portion 114 of the housing 102.

Figure 8C:
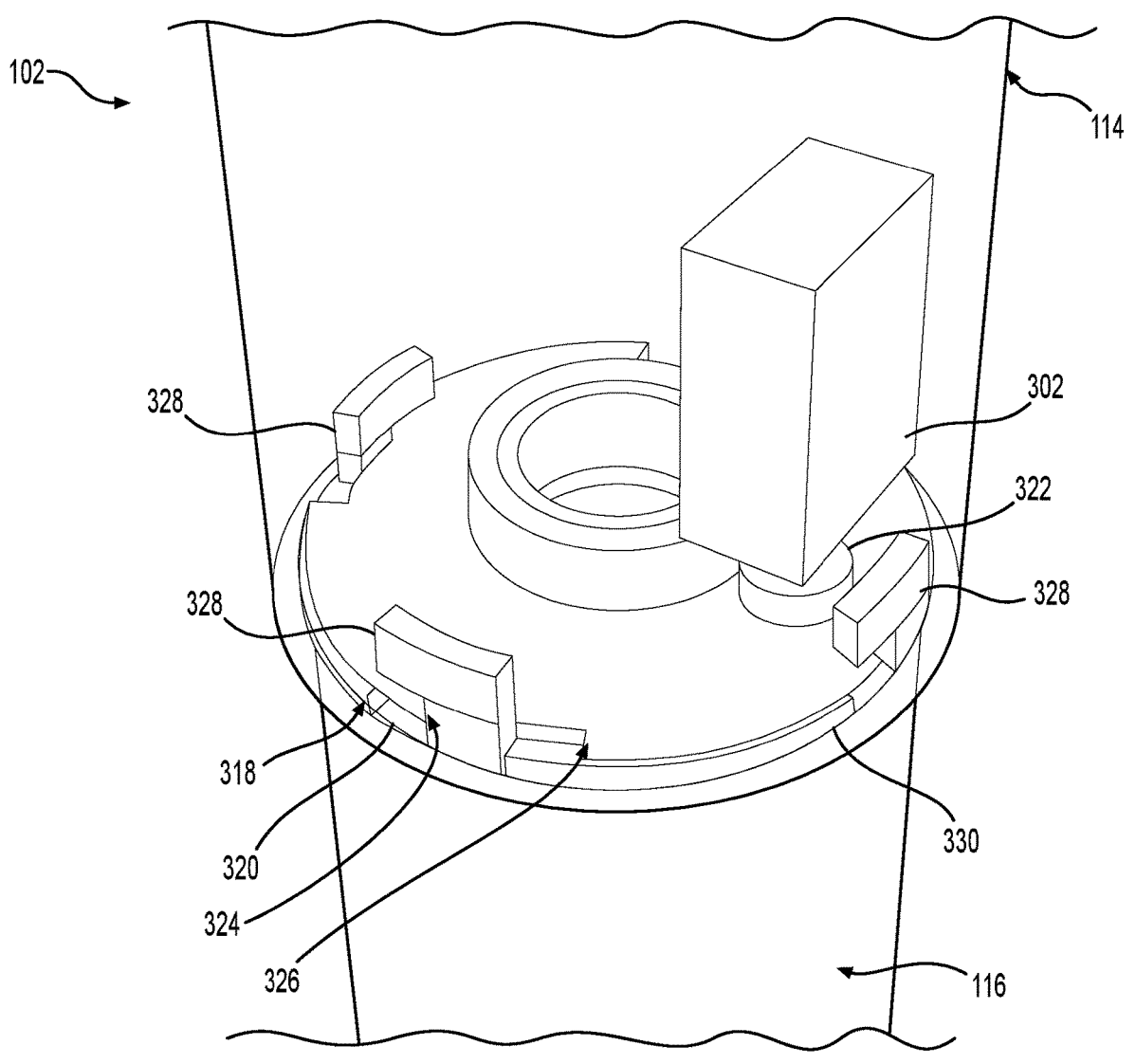
FIG. 8C is a top perspective view of an embodiment of the first and second portions of the housing in a locked position.

To reach the locked position shown in FIG. 8C, the motor 302, upon receiving an electrical signal from the printed circuit board 126, rotates the second gear 322, which rotates the disc 324. The disc 324 rotates such that the cutouts 326 are no longer aligned with the L-shaped flanges 328. Therefore, the L-shaped flanges 328 and consequently, the second portion 116 of the housing 102, cannot be removed from the first portion 114. In some embodiments, the disc 324 is spring loaded such that the locked position is the default position of the disc 324.

The circuitry described to activate the locking mechanism may also be connected to one or more signal LEDs 130 on the housing 102, as shown in FIG. 1. In one embodiment, the signal LEDs 130 illuminate when the solenoid 124 is activated and the dispensing device 100 is in the locked position. In an alternative embodiment, the signal LEDs 130 may illuminate with color, such as red, when the solenoid 124 is activated and the dispensing device 100 is in the locked position, and green when the solenoid 124 is deactivated or otherwise inactive and the dispensing device 100 is in the unlocked position.

The circuitry also connects to and powers the screen 112 within the recess 110 on the housing 102. In the embodiments shown in FIGS. 2 and 3A, the recess 110 is enclosed by a lens 132. The lens 132 protects the screen 112 from liquid, debris, and other contaminants while still allowing a user to view the screen 112 clearly. In the depicted embodiment, the lens 132 is flush with the housing 102 to allow the user to easily manipulate the dispensing device 100. In one embodiment, the lens 132 may comprise a biometric sensor therein. In alternative embodiments, such as that shown in FIG. 1, the biometric sensor 134 is at a separate location along the housing 102. The biometric sensor 134 may include a fingerprint scanner, an iris scanner, a heart rate detector, and the like. The lens 132 may also comprise touchscreen capabilities such that the user may enter a passcode on a keypad displayed on the screen 112. The biometric sensor 134 and passcode elements provide an additional layer of security for access to the medication verifying the individual using the device and sending a signal to the printed circuit board 126 to move the solenoid 124 into the unlocked position.

In some embodiments, the dispensing device 100 may further comprise a photocell 136 located within the housing and connected to the circuitry. The photocell 136 detects light conditions inside the device. Thus, the photocell 136 can detect when the dispensing device 100 is tampered with or broken into. In other embodiments, the dispensing device 100 may further comprise a medication sensor 138 connected to the circuitry that monitors the level of medication in the liquid container 118. Thus, the medication sensor 138 can send a signal to the printed circuit board 126 when the liquid container 118 is empty or has a low volume of medication remaining.

The pump assembly 120 may additionally comprise a tactile switch 140. The tactile switch 140 operates as a momentary switch that it is activated when the pump assembly 120 is fully actuated. The tactile switch 140 is operably connected to the printed circuit board 126 where full actuations of the pump assembly 120 are recorded. Circuity from the printed circuit board 126 additionally extends to a real-time clock chip 142. The real-time clock chip 142 can be used to provide the date and time for display on the screen 112. As will be discussed later, the real-time clock chip 142 can also be used in conjunction with the solenoid 124 and tactile switch 140 to lock the dispensing device 100.

Figure 4:
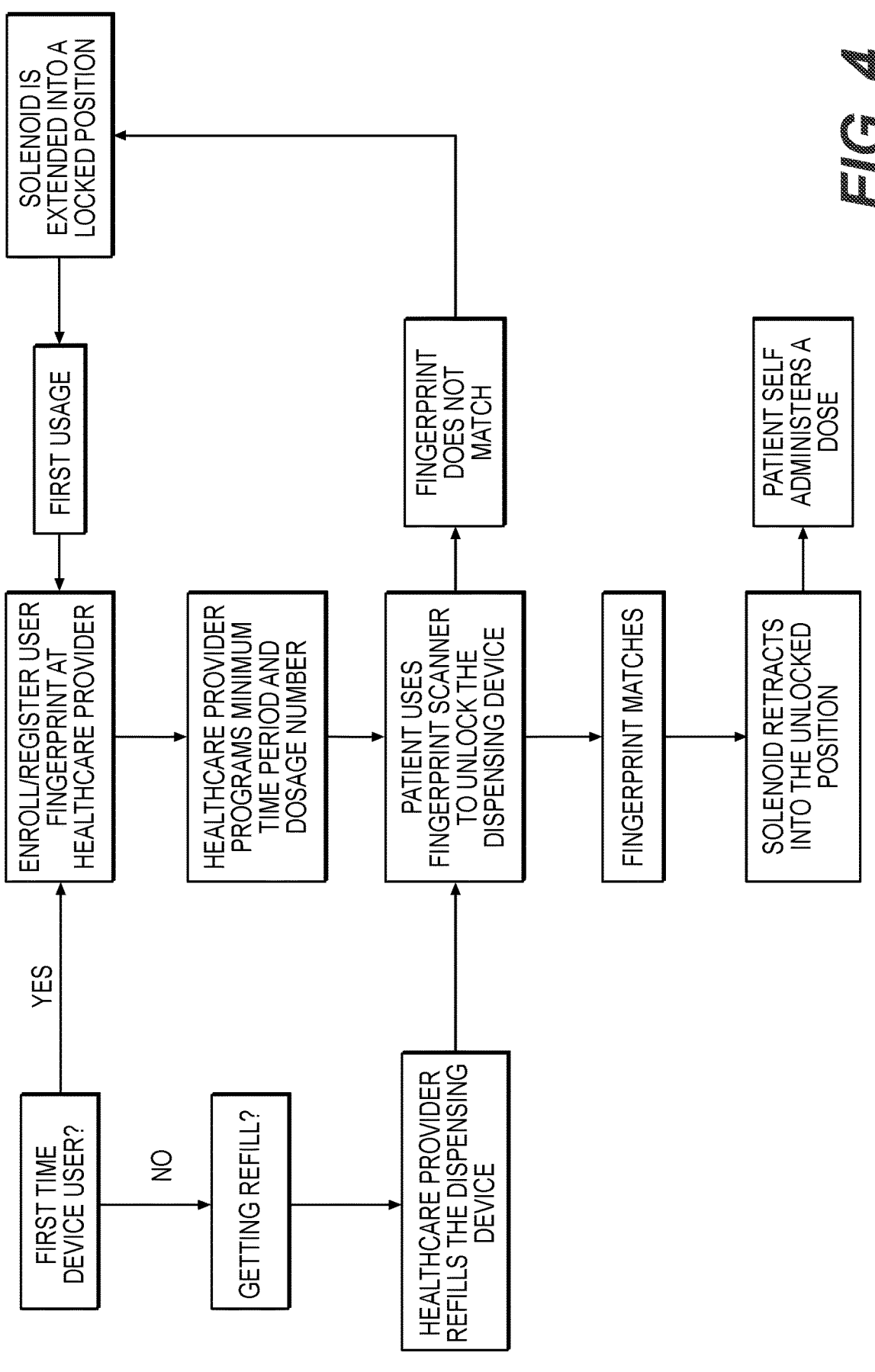
FIG. 4 is a diagram representation of an embodiment of the method according to the present invention.
Figure 5:
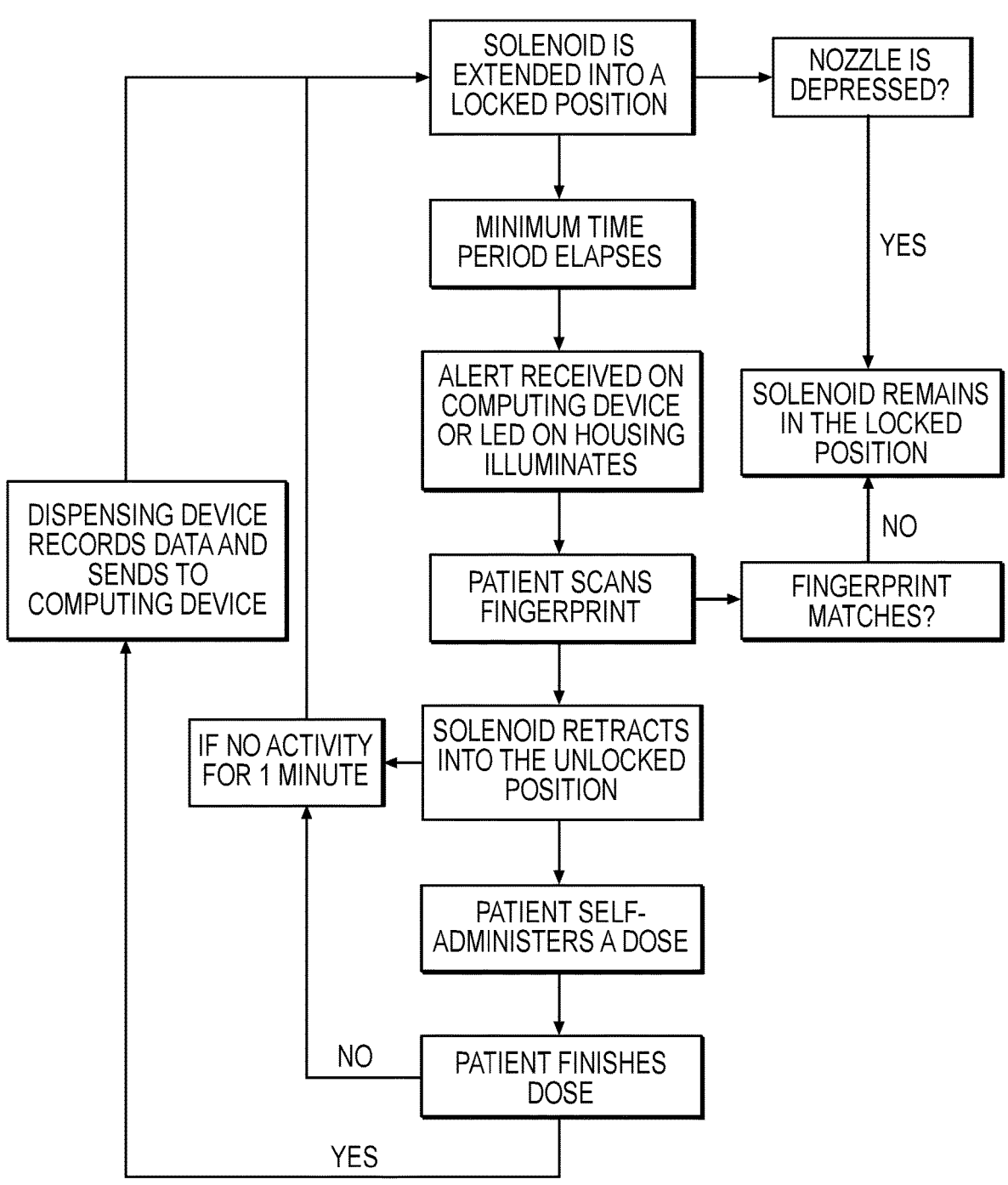
FIG. 5 is a diagram representation of an embodiment of the method according to the present invention.
Figure 6:
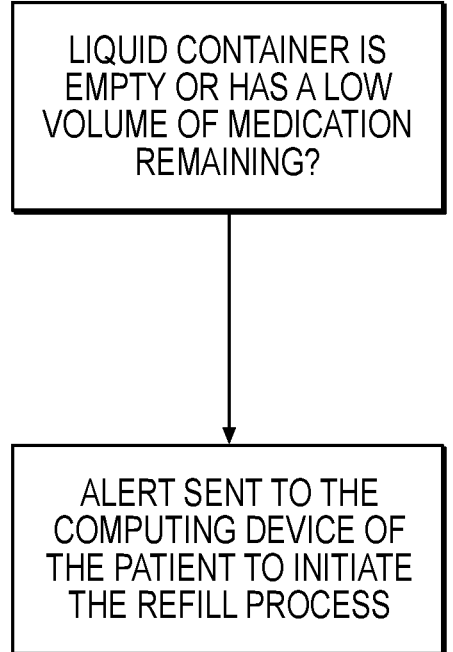
FIG. 6 is a diagram representation of an embodiment of the method according to the present invention.

Referring now to FIGS. 4-6, there are shown diagram representations of an embodiment of the method according to the present invention. In use, the components in the dispensing device 100 can communicate with a web platform accessible on the computing device 200 to control the dispensing of medication. The printed circuit board 126 may utilize Bluetooth low energy (BLE) as a wireless protocol to communicate with the computing device 200. Thus, the printed circuit board 126 can be programmed from the computing device 200. For example, a healthcare provider may adjust setting on the web platform via a terminal on a computing device 200. The healthcare provider may indicate a dosage number for the medication stored in the liquid container 118 and a minimum time period between dosages. This information is then transmitted to the printed circuit board 126. The printed circuit board 126 calculates the dosage number based on feedback from the tactile switch 140 and determines the time period between dosages based on data from the real-time clock chip 142.

In addition to programming the dispensing device 100, the web platform may be utilized by the healthcare provider to view status information from the dispensing device 100. For example, the dosage time, lock status, tamper alerts, and dosages remaining are information that may be pushed via a wireless network and/or cellular data from the dispensing device 100 to the web platform, which is ultimately accessible by the healthcare provider at a terminal on the computing device 200. In addition, the web platform may also include a calendar interface, or other scheduling format, for tracking patient dosages and prescription regimens. Thus, the dispensing device 100, the healthcare provider's computing device 200, and a patient's smartphone (as explained below) may exchange status information via GSM or some other similar digital cellular network.

The biometric sensor 134 may be programmed by the patient in the presence of the healthcare provider. For example, the healthcare provider can adjust settings on the web platform to allow for programming of the biometric sensor 134. The biometric sensor 134 can then scan the fingerprint of the patient, for example, to assign the patient identity to the particular dispensing device 100. Once programmed, the biometric sensor 134 will require identity verification before the dispensing device 100 can be used.

Once the dispensing device 100 is programmed via the web platform on the healthcare provider's computing device 200, the patient may use the dispensing device 100. To access the medication, the patient will first prove his or her identity by actuating the biometric sensor 134, such as placing a finger on the biometric sensor 134 for fingerprint scanning verification. Once the patient's identity is verified, the patient can self-administer the first dose of medication.

In an alternative embodiment, the patient's smartphone or other computing device may serve as a second layer of authentication to utilize the dispensing device 100. For example, the patient may have access to a patient interface of the web platform on his or her smartphone. At the dosing time, the patient may be required to authenticate himself or herself via the smartphone. For example, the patient may complete authentication by unlocking his or her phone via a passcode or fingerprint sensor. In another embodiment, the healthcare provider may send a temporary or one-use PIN code from the healthcare provider interface of the web platform to the patient interface of the web platform. Therefore, the patient can access the web platform on his or her smartphone, retrieve the PIN code, and enter the PIN code on the dispensing device 100 to unlock it.

To administer the first dose, the patient holds the dispensing device 100 such that the nozzle 108 is close to or partially within the nostril and applies pressure to the nozzle 108 towards the surface 104a of the first closed end 104. The pump assembly 120 expels medication from the nozzle 108 such that the patient may inhale the medication. When the pump assembly 120 is actuated, the tactile switch 140 is also triggered. The tactile switch 140 sends a signal to the printed circuit board 126 that the pump assembly 120 has been actuated, indicating that a dosage has been administered. Simultaneously, the printed circuit board 126 associates the signal from the tactile switch 140 with the time provided by the real-time clock chip 142.

If the healthcare provider has set a minimum time period between dosages, receipt of the signal from the tactile switch 140 will also cause the printed circuit board 126 to actuate the solenoid 124. The solenoid 124 will move into the path of the nozzle 108 thereby preventing the patient from administering a subsequent dose of medication. The dispensing device 100 will remain in the locked position with the solenoid 124 blocking the actuation of the nozzle 108 until the minimum time period has elapsed. The printed circuit board 126 can monitor the time using data received from the real-time clock chip 142. Once the minimum time period has elapsed after actuation of the tactile switch 140, the printed circuit board 126 will trigger the solenoid 124 to retract thereby allowing the patient to fully depress the nozzle 108 to administer a subsequent dosage. Thereafter, the locking process is repeated.

In embodiments wherein one or more signal LEDs 130 are located on the housing 102, the signal LEDs may illuminate a red color when the solenoid 124 is in the path of the nozzle 108, indicating that a dosage may not be administered, and a green color when the solenoid 124 is retracted, signaling to the patient that a subsequent dosage is available. As the printed circuit board 126 can wirelessly communicate with a computing device 200, a signal from the printed circuit board 126 can be transmitted to the computing device 200 alerting the patient that the next dosage is available. In an alternative embodiment, the medication sensor 138 may transmit a signal to the printed circuit board 126 and ultimately to the computing device 200 indicating that the liquid container 118 is empty or has a low volume of medication remaining. This alerts the patient to initiate the process of refilling the prescription.

In embodiments wherein the housing 102 comprises a photocell 136, the photocell 136 can be configured to send a signal to the printed circuit board 126 when the photocell 136 detects light above a programmed threshold. The printed circuit board 126 can be programmed to transmit a signal to a computing device 200 accessible by the healthcare provider. The signal can manifest as an alert on the web platform notifying the healthcare provider that the dispensing device 100 has been tampered with. In additional embodiments, the printed circuit board 126 may be programmed to send data from any component or combination of components of the dispensing device 100 to a computing device 200 operated by the healthcare provider and/or by the patient. The healthcare provider and the patient can then access this data to improve compliance with the treatment plan.

Figure 17:
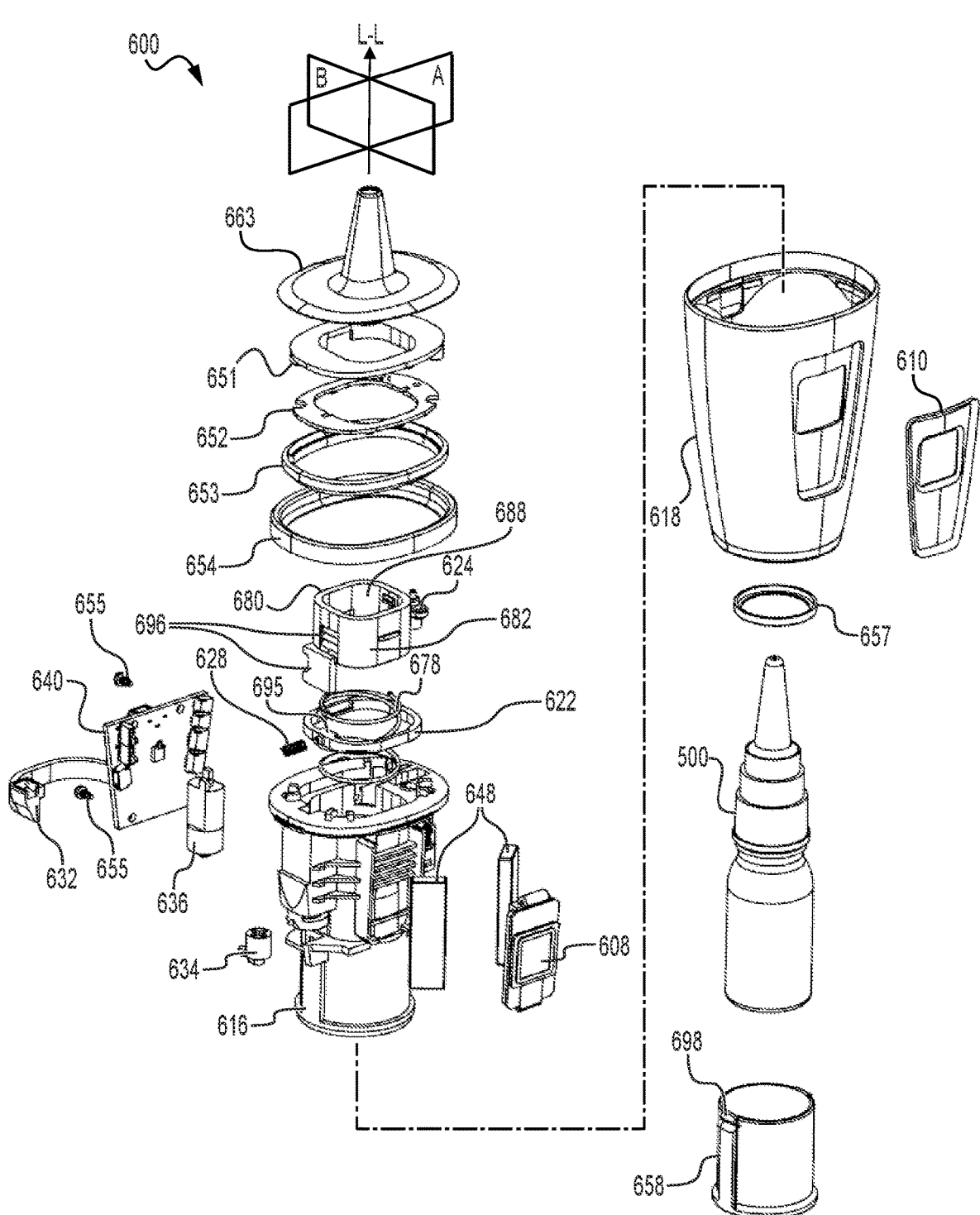
FIG. 17 is an exploded view of another embodiment of a dispensing device according to the present invention.
Figure 18:
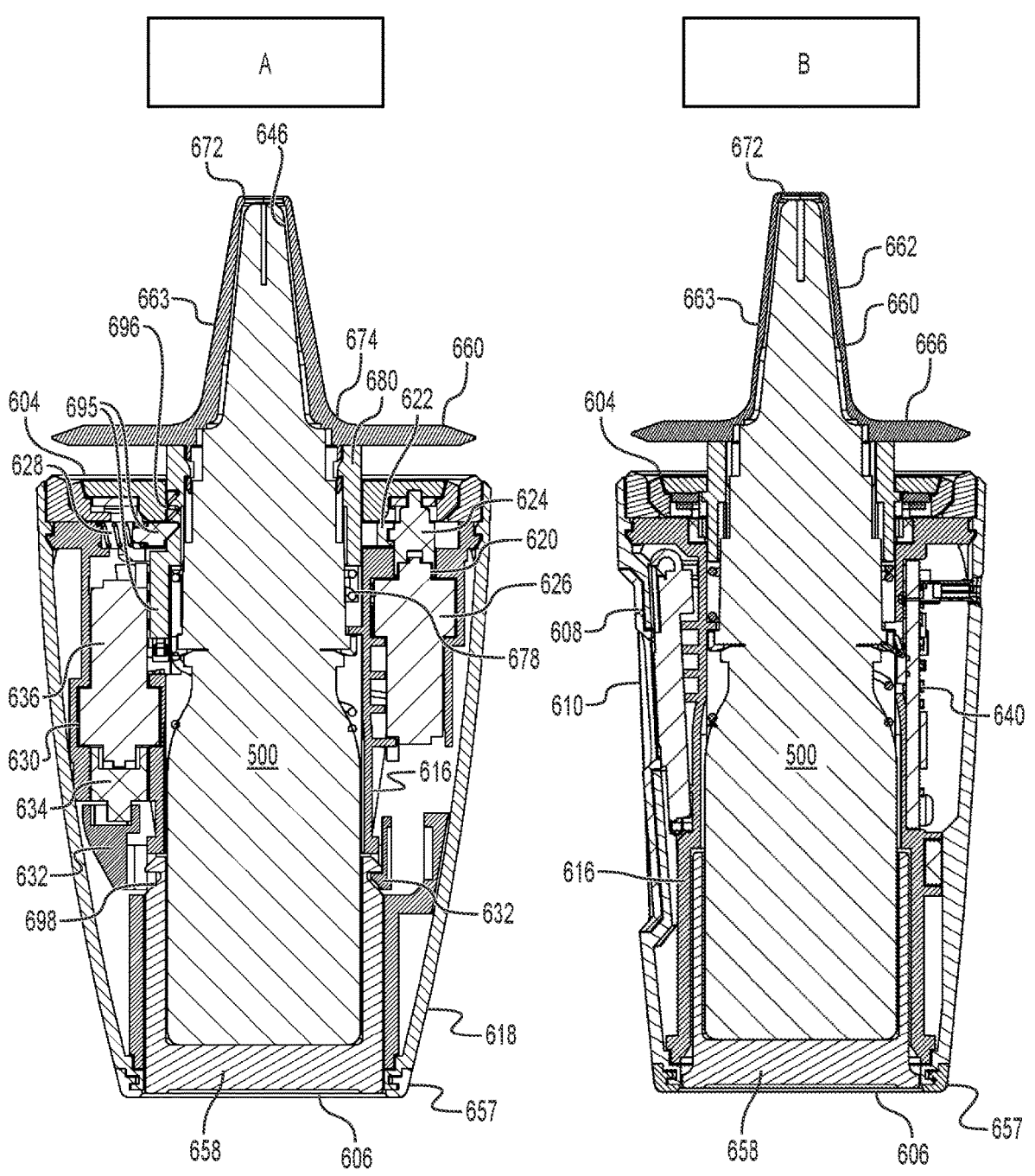
FIG. 18A is a cross-sectional view of the dispensing device illustrated in FIG. 17 cut along plane A according to the present invention.
FIG. 18B is a cross-sectional view of the dispensing device illustrated in FIG. 17 cut along plane B according to the present invention.

FIGS. 9 through 15 and also FIGS. 17, 18A, and 18B respectively illustrate two additional embodiments of the dispensing device 400, 600. Components and/or design strategies of the various dispensing device embodiments 100, 400, 600 are combinable or exchangeable as understood by a person skilled in the pertinent art according to the teachings of the present disclosure. For instance, although not explicitly illustrated, the additional embodiments 400, 600 can include the signal LEDs 130, lens 132, screen 112, photocell 136, medication sensor 138, tactile switch 140, real time clock 142, any combination thereof, or variations thereof. Likewise, the additional embodiments 400, 600 can include appropriate electrical circuitry and mechanical structures to support such components.

One of the embodiments 400 as illustrated includes sensors 442, 444, 446 (FIG. 14B) and visual features 490, 492, 494 (FIG. 10) for detection of a level of depression of the nozzle 460. Such sensors and visual features can be incorporated into other dispensing device embodiments 100, 600 illustrated herein, or a variation thereof, as understood by a person skilled in the pertinent art according to the teachings of the present disclosure. The dispensing device 100, 400, 600 can be configured to lock the nozzle 108, 460, 660 when the nozzle is partially depressed for a prolonged period of time, and/or when a user performs a partial depression and returns the nozzle to a fully extended position. This prevents the user from administering multiple partial doses in an attempt to bypass the security of the dispensing device 100, 400, 600.

Figure 13:
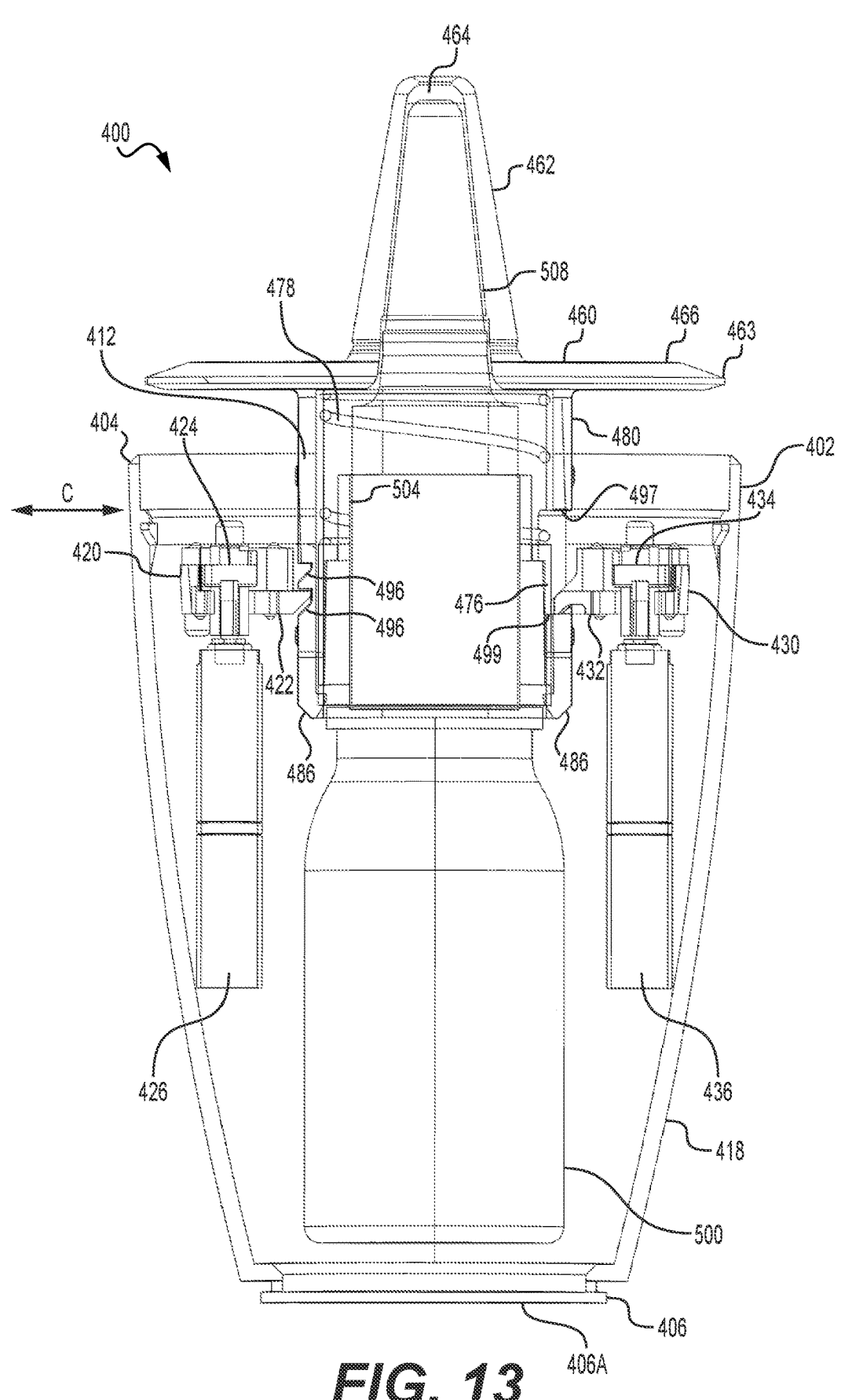
FIG. 13 is a cross-sectional view of the dispensing device as illustrated and oriented in FIG. 9 with components removed to visualize a dose lock and a vial lock according to the present invention.

The dispensing device 100, 400, 600 can further including a ratcheting dose lock such as dose lock 420 illustrated in FIG. 13 and dose lock 620 illustrated in FIG. 18A. The illustrated dose locks 420, 620 are ratcheted to allow the nozzle 460, 660 to return to the completely extended position and inhibit the nozzle from being further depressed when the dose lock 420, 620 is in the locked position and the nozzle is partially depressed. Alternatively, the ratchet can be shaped to allow the nozzle to be depressed and inhibit extension of the nozzle. Each design has certain advantages. For instance, the lock-out ratchet (which inhibits depression of the nozzle) prevents further administration of the medication immediately when the lock is engaged, which may be a desired functionality if prevention of administering too much medication is of primary concern. The dose-forcing ratchet (which inhibits extension of the nozzle) prevents a partial depression from occurring when the lock is engaged, but may not prevent completion of a dose, which may be desired functionality if prevention of small doses is of primary concern.

The additional embodiments 400, 600 can function together with one or more computing devices such as the computing device 200 illustrated in FIG. 1, other computing devices disclosed herein, and/or one or more computing devices as understood by a person skilled in the pertinent art according to the teachings of the present disclosure. The dispensing devices 400, 600 can be used to execute methods illustrated in FIGS. 4 through 6. The dispensing devices 400, 600 can connect directly and/or remotely to a computing device (e.g. the illustrated computing device 200) via Wi-Fi/, Bluetooth, cellular, and the like to control the dispensing device 400, 600 (lock/unlock, load biometrics/load new nasal spray device/change dosing schedule). The dispensing devices 400, 600 can communicate to the computing device 200 to alert a physician via push notifications if patient has missed a dose or tampering with device. The dispensing device 400, 600 can be configured (e.g. by a physician) to generate an output to remind the patient when to dose. The output can be many different outputs known in the art, including, but not limited to a light, display, sound, or other alert or communication to another device such a patient's mobile phone. The dispensing devices 400, 600 can further monitor patient usage of the dispensing device 400, 600 and provide information/data related to the patient usage to a computing device 200, directly via a display on the device 400, 600, or other means to inform the physician regarding patient adherence to prescription. The dispensing device 400, 600 can have a timed lockout (preset by Dr), and/or scheduled lockout. The timed lockout can be preset by an authorized user (e.g. physician). The scheduled lockout can be set and/or edited remotely via a web platform (or other networked platform) accessible via a physician's computing device.

Both options still require patient credentials to unlock the device. This can be done using the biometric scanner on the device, or in future using the biometric (finger/facial/eye) scanning ability on the user's mobile phone.

Generally, the dispensing devices 400, 600 provide secure drug delivery and include a disposable part containing the drug and a reusable exoskeleton or housing component. The exoskeleton secures the disposable part containing the drug/medicine and controls when and how the substance is dispensed. In some embodiments, the exoskeleton is able to secure (e.g. encapsulate) standardized nasal spray devices 500. The exoskeleton can lock and unlock the nozzle movement of the standardized nasal spray 500. The locking and unlocking of the device 400, 600 (dosing) can be controlled and/or configured remotely (Wi-Fi/BT) via a mobile phone app and web platform, as prescribed by a Doctor/Physician. The nozzle can include lock details that interface with the exoskeleton lock mechanisms.

A standardized nasal spray device/vial 500 can be inserted into the exoskeleton from locations, including, but not limited to the top (see the dispensing device 400 illustrated in FIGS. 9 through 15) and bottom (see the dispensing device 600 illustrated in FIGS. 17, 18A, and 18B). The top loading dispensing device 400 can include a nozzle 460 that is separable from the housing 402. The nozzle 460 can be disposable and can be attached to the standardized nasal spray. Alternatively, a custom disposable vial can be constructed including a nozzle portion following the design strategies of the disposable nozzle 460. Because the nozzle 460 of the top-loading dispensing device 400 is disposable, the nozzle 460 can be disposed and/or cleaned separately from the reusable housing 402 of the device 400, thereby potentially provider better hygiene compared to the bottom-loading dispensing device 600. The bottom-loading device 600 can be configured to receive a standard vial 500 without requiring a specialized nozzle 460, and therefore can potentially provide convenience and/or cost savings over the top-loading device 400.

The dispensing devices 400, 600 can include sensors (e.g. optical/imaging) to detect nozzle movement and device tampering, micro movement sensors to detect user specific movement patterns to detect when a different user handles the device 400, 600, and/or a drug neutralizer (e.g. powder or sponge) to chemically neutralize drugs released from the internal vial 500. As discussed above and as those skilled in the pertinent art would appreciate, one or more of these features can also be combined and/or interchanged with features of device 100.

Specifics of each additional embodiment 400, 600 will now be discussed in relation to the figures.

Figures 9, 10:
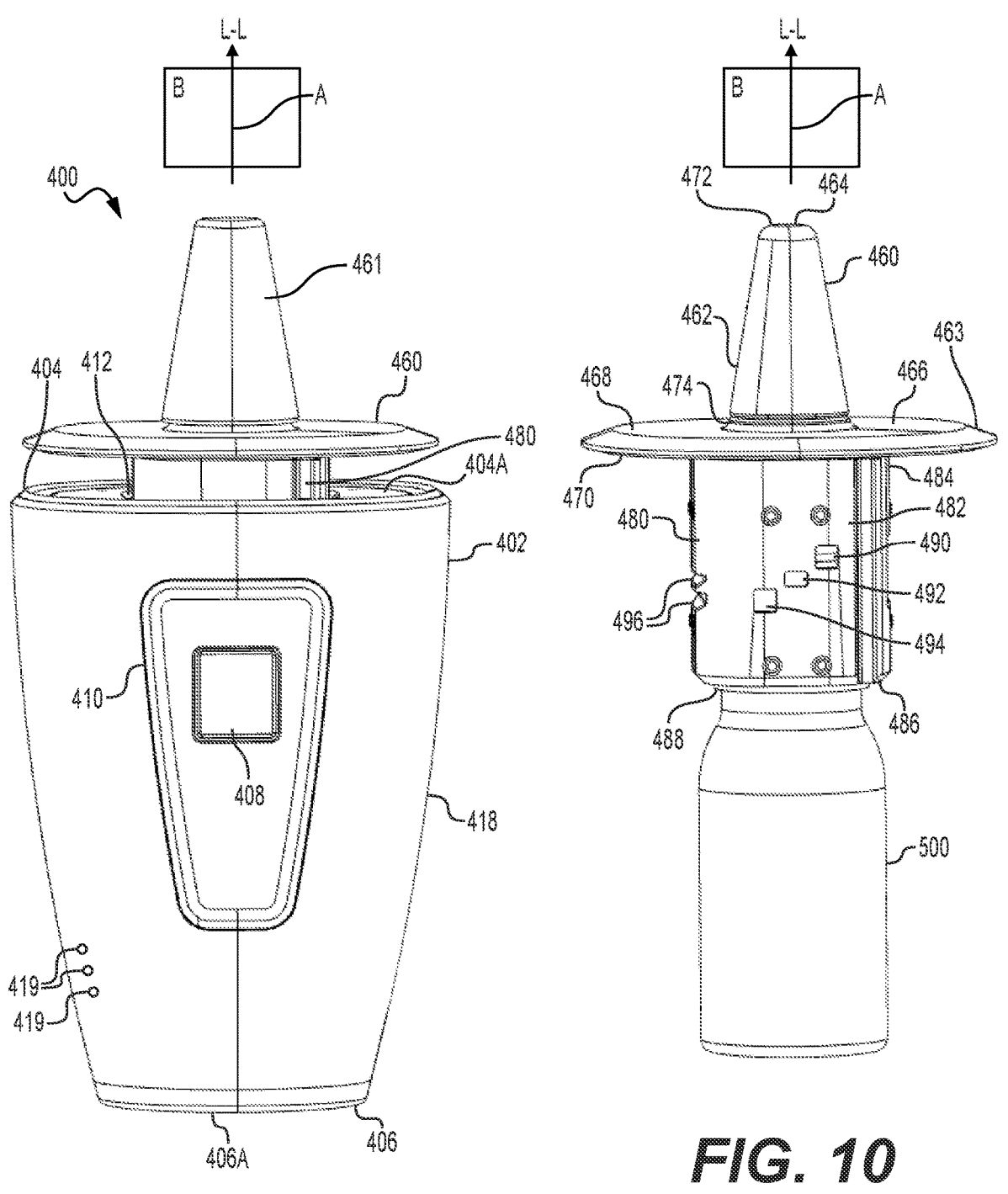
FIG. 9 is a profile view of another embodiment of a dispensing device according to the present invention.
FIG. 10 is a profile view of a nozzle and vial according to the present invention.

FIG. 9 is a profile view a top-loading dispensing device 400 according to the present invention. The dispensing device 400 includes a housing 402 and a nozzle 460 that together form an exoskeleton surrounding (at least partially) and securing a vial 500 (FIG. 10).

The nozzle 460 and vial 500 illustrated in FIG. 10 are snapped together. The nozzle 460 includes a housing interface 480 that snaps onto the vial 500, allowing the nozzle 460 to be depressed, and providing features thereon for locking the combined nozzle 460 and vial 500 into the housing 402. The combined nozzle 460 and vial 500, whether mated during or post-production, can function to deliver medication both with and without the housing 402, which allows health care providers to choose whether a specific patient, when given a particular medication, is provided the medication in the housing 402 or not. Because the nozzle 460 is not integral to the housing 402, the nozzle 460 can be disposed of, or cleaned separately from the housing 402, thereby potentially providing a more hygienic product compared a reusable dispensing device with an integral nozzle. Further, the opening 412 through which the nozzle 460 slides during operation is the same opening from which the vial is removed, eliminating the need for a second opening for vial removal. Without a second opening for vial removal, the cover 418 of the housing 402 can have a smoother, and therefore potentially more tamper resistant outer surface.

The device 400 is oriented vertically about a longitudinal axis L-L intersected by orthogonal planes A, B. The housing 402 has a first, top end 404 with a first, top surface 404*a* orthogonal to the longitudinal axis L-L and planes A, B. The housing 402 has a second, bottom end 406 with a second, bottom surface 406*b* substantially parallel to the first surface 404*a*. The nozzle 460 extends perpendicular from the top surface 404*a* of the housing 402. The housing 402 has an opening 412 on the top surface 404*a*, and the nozzle 460 has a housing interface 480 configured to be positioned within the opening 412 and slidably engage the housing 402. When the nozzle 460 is slidably engaged to the housing 402 as illustrated, and the nozzle 460 is unlocked, the nozzle 460 is translatable from a completely extended position as illustrated in FIG. 9 to a completely depressed position where a bottom surface 470 of an engagement ring 466 of the nozzle 460 approaches the top surface 404*a* of the housing 402 similar to the depressed position of nozzle 108 in relation to housing surface 104*a* as illustrated in FIG. 2.

As used herein, the terms "completely extended position" and "completely depressed position" refer to the extremes between which the nozzle moves for its intended purpose of providing a dosage.

The housing 402 can further include a biometric sensor 408 which can function similar to the biometric sensor 134 described elsewhere herein. For instance, a fingerprint scan on the sensor 408 can be used by electrical circuitry of the device 400 to determine whether to unlock the dose lock. Additionally, or alternatively, a fingerprint scan on the sensor (e.g. by a physician) can be used by electrical circuitry of the device 400 to determine whether to unlock the vial. The housing 402 can include a finger cover 410. The finger cover 410 can include a display, and/or a display can be positioned elsewhere on the housing 402.

The display can function similar to the display 112 described elsewhere herein.

The device 400 can further include a removable nozzle cap 461.

FIG. 10 is a profile view, in the same orientation as FIG. 9, of the nozzle 460 engaged to a medicinal vial 500. Referring collectively to FIGS. 9 and 10, the nozzle 460 and vial 500 as assembled in FIG. 10 are removable from the housing 402 in FIG. 9 without damaging the housing 402, and preferably without damaging the nozzle 460. During usage, the nozzle 460 and vial 500 are replaceable and preferably disposable. The housing 402 can be reloaded with a new nozzle 460 and vial 500 assembly. The medicinal vial 500 can be loaded via the opening 412 in the top surface 404*a* of the housing 402. The housing 402 therefore includes a chamber 414 (FIG. 13) sized to receive the medicinal vial 500, and the chamber 414 is accessible via the opening 412 in the top surface 404*a* of the housing 402.

The outer surface of the housing 402, when assembled to the nozzle 460 can be completely devoid of fasteners or other externally accessible avenues for opening the device 400. In some applications it can be desirable to provide draining holes 419 to allow liquids which have been released from the vial 500 in the device 400 to exit the device 400. In other applications, it can be desirable to capture liquids released from the vial 500 within the device 400 (e.g. a sponge in the chamber 414 illustrated in FIGS. 14A and 14B).

Figures 11A, 11B, 12:
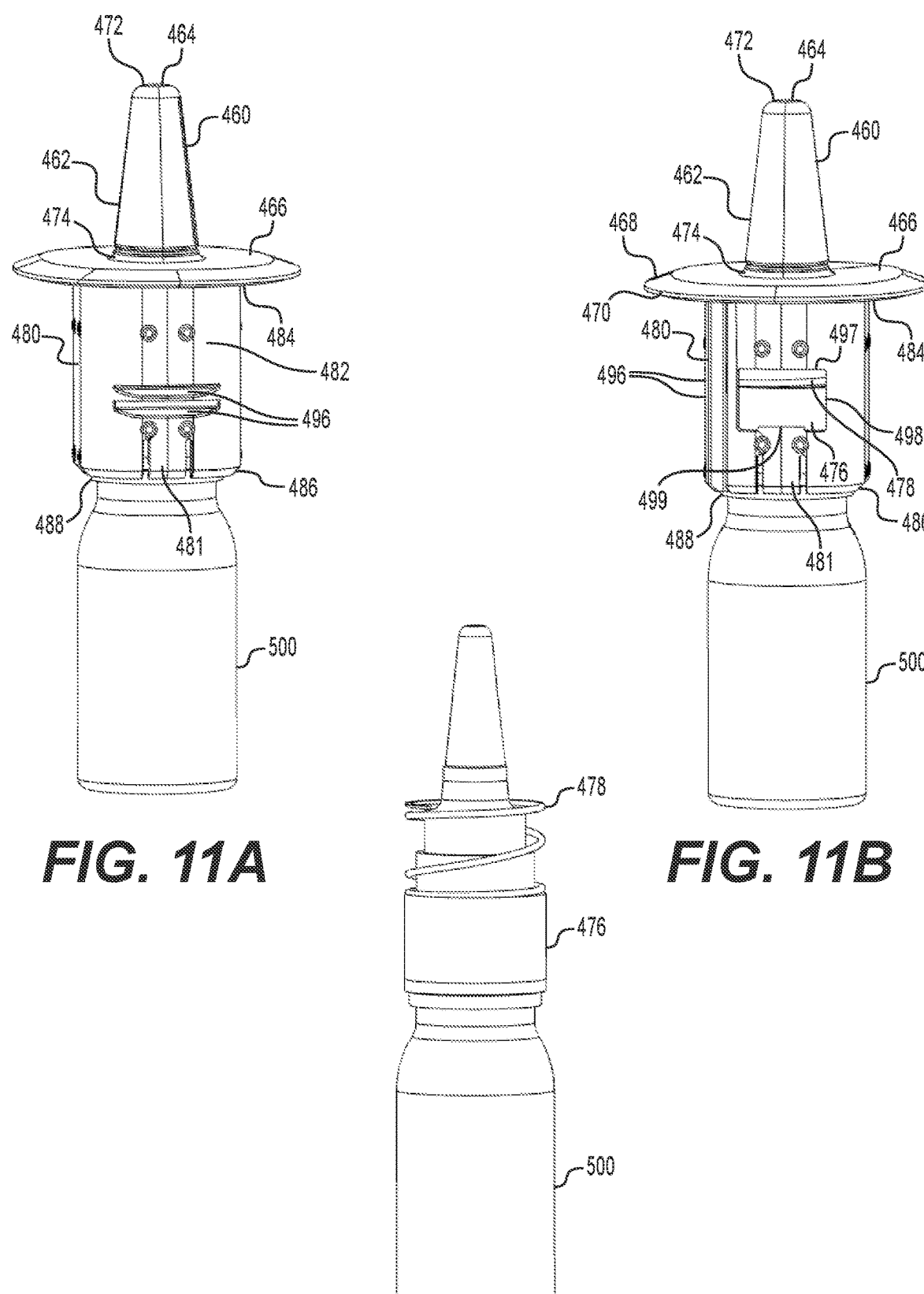
FIGS. 11A and 11B are orthogonal profile views of the nozzle and vial illustrated in FIG. 10 according to the present invention.
FIG. 12 is a profile view of the vial, retention ring, and spring according to the present invention.

FIGS. 11A and 11B are orthogonal profile views of the nozzle 460 and vial 500 where FIG. 11A is looking onto the left side of the assembly illustrated in FIG. 10 and FIG. 11B is looking onto the right side of the assembly illustrated in FIG. 10. FIG. 12 is an illustration of the assembly illustrated in FIGS. 10, 11A, and 11B with the nozzle 460 removed. Referring collectively to FIGS. 10, 11A, 11B, and 12 the nozzle 460 includes a conical portion 462, an engagement ring 466, and a housing interface 480, a spring 478, and a retention ring 476. Preferably, the conical portion 462, engagement ring 466, and housing interface 480 are molded as a single piece, handle portion 463. Alternatively, at least one of the conical portion 462, engagement ring 466, and housing interface 480 can be individually molded and affixed together to form the handle portion 463.

The conical portion 462 has a dispensing end 472, a base end 474, and a fluidic passageway 464 extending along the longitudinal axis L-L through the base end 474 and dispensing end 474. The engagement ring 466 extends radially from the base end 474 of the conical portion to provide a top surface 468 against which a user can provide a force to depress the nozzle 460. A bottom surface 470 of the engagement ring 466 faces away from the dispensing end 472. The bottom surface 470 can further be shaped or otherwise configured to contact the top surface 404*a* of the housing 402, when the device 400 is assembled, to inhibit further depression of the housing interface 480 into the housing 402. The housing interface 480 has an outer surface 482 that circumscribes the longitudinal axis L-L, an upper end 484 affixed to the engagement ring 466, an open lower end 486, a passageway 488 extending between the upper end 484 and lower end 486. A vial 500 and nozzle 460 assembled during production, because it is pre-assembled, does not require any further assembly on the part of the health care provider, and therefore provides greater convenience.

The nozzle 460 can be fitted to the vial 500 by first placing the retention ring 476 and spring 478 over the vial 500 and then sliding the housing interface 480 over the spring and retention ring 476. The housing interface 480 can include flexible hooks 481 that extend to move over the vial 500 and snap under a ridge on the vial to engage and secure the nozzle 460 to the vial 500. The interior of the conical portion 462 and engagement ring 466 can be shaped to fit over the vial nozzle. The vial and nozzle assembly can further include an adapter or vial nozzle cover to aid in mating the nozzle 460 to the vial 500. In this way, the nozzle 460 can be fit over existing standard sized vials. Alternatively, the vial 500 and nozzle 460 can be specially designed in concert and/or integrated.

The nozzle 460 includes features that function together with the housing 402 to control dispensing of a drug in the vial 500 as described in greater detail below. As illustrated in FIGS. 10, 11A, and 11B, the drug can also be dispensed when the nozzle 460 and vial assembly are outside of the housing. This can allow drugs, whether they are intended to be regulated during usage or not, to be packaged identically, adding convenience, and potentially saving cost.

Referring to FIG. 10, the housing interface includes openings 490, 492, 494 in the outer surface 482 to aid in detecting partial depression of the nozzle 460. As the nozzle 460 is depressed over the vial 500, movement of the housing interface 480 in relation to a portion of the nozzle 460, such as the retention ring 476, is visible through the openings 490, 492, 494. The housing 402 can include one or more sensors to detect movement of the portion of the nozzle 460 (e.g. retention ring 476) over the openings 490, 492, 494. FIG. 10 illustrates three openings 490, 492, 494 positioned such that three positions of depression of the nozzle 460 are detectable. The housing interface 480 can include one or more such openings 490, 492, 494 to serve the same purpose, where the maximum number of openings is limited by physical design constraints as understood by a person skilled in the pertinent art according to teachings of the present disclosure. Preferably, the outer surface 482 of the housing interface 480 is visually in high contrast with the retention ring 476 so that the retention ring 476 can be easily visualized in relation to the housing interface 480 by optical sensors. When the nozzle 460 and vial 500 assembly is installed in the housing 402, the retention ring 476 is substantially stationary in relation to the optical sensors while the openings 490, 492, 494 move to cover and uncover the optical sensors' view of the retention ring 476. Optical sensors check for movement at the start of the dose and at the end of a dose by detecting movement of the top and bottom openings 490, 494 on the housing interface 480. If a dose is started but not pushed all the way to the bottom the dose lock 420 will engage (described in greater detail in relation to FIGS. 13 and 14B).

As illustrated in FIGS. 10 and 11A, the housing interface 480 includes indentations 496 for locking depression of the nozzle 460 into the housing 402, i.e. inhibiting a user from receiving a dose. Two indentations 496 are illustrated. The lower indentation is positioned to maintain the nozzle at a completely extended position when the housing interface 480 is slidably engaged to the housing 402.

Figure 14A:
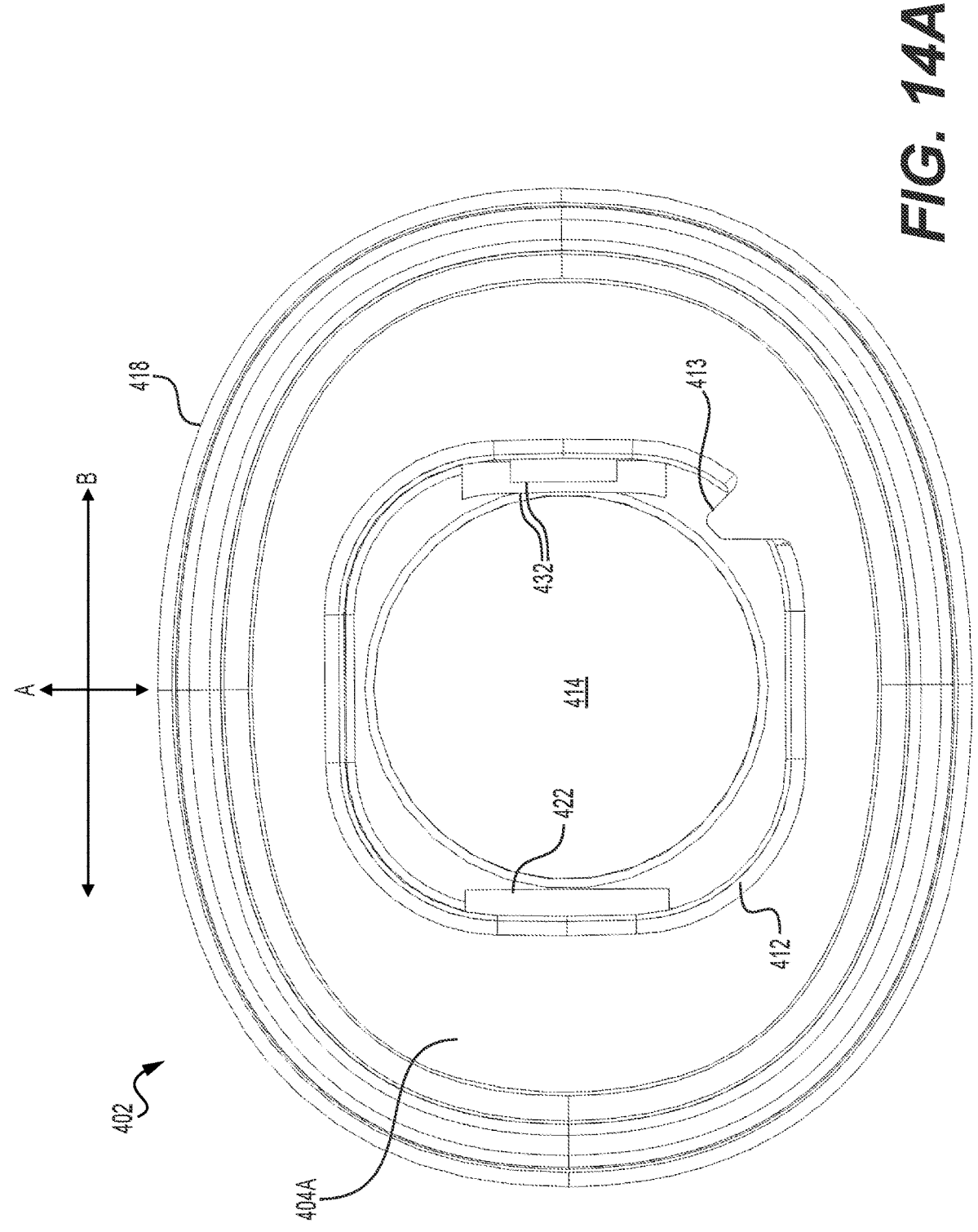
FIG. 14A is a top view of a housing according to the present invention.
Figure 14B:
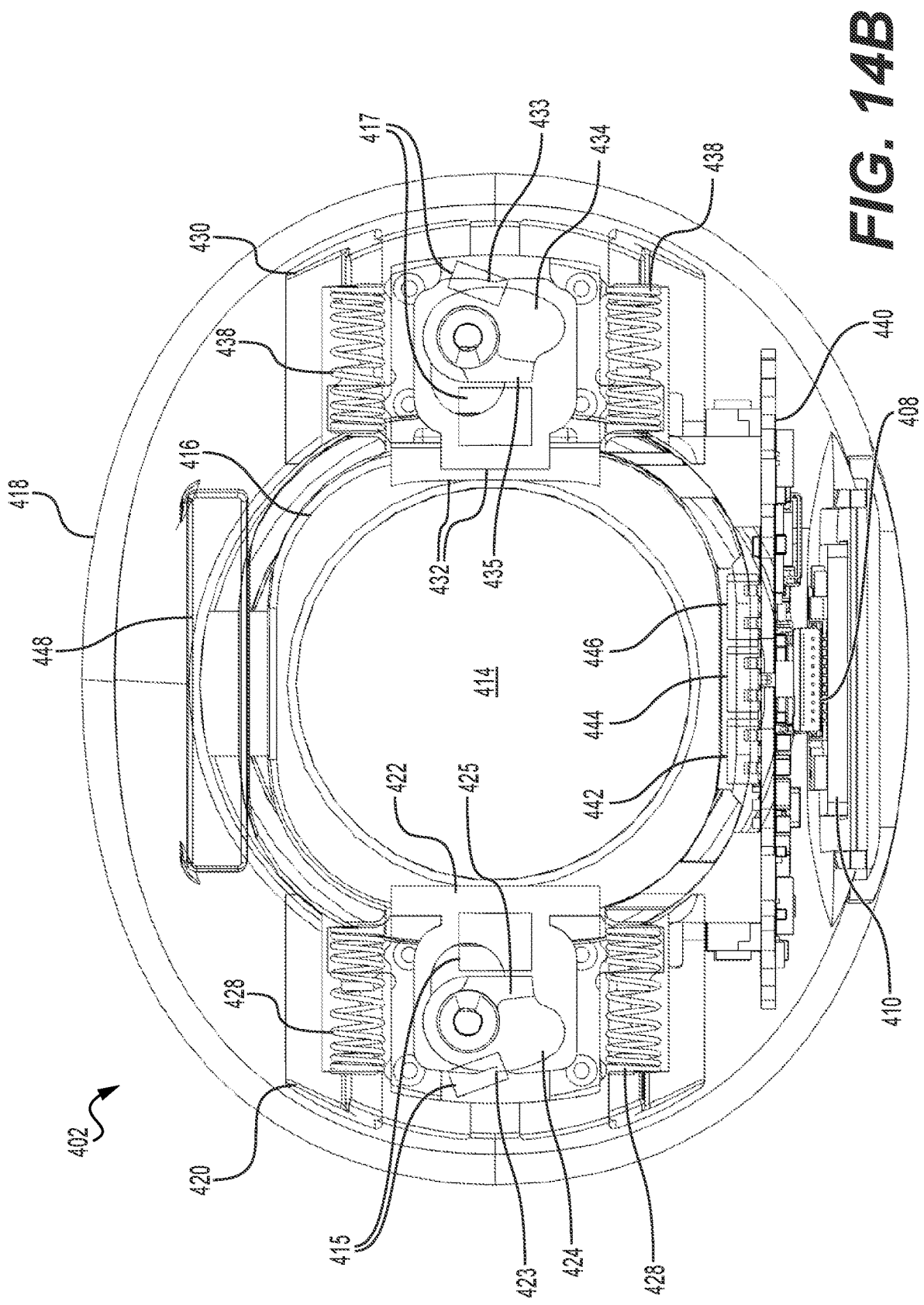
FIG. 14B is a cross-sectional view of the housing as oriented in FIG. 14A according to the present invention.

FIGS. 13 and 14B illustrate the housing dose lock 420 which engages the indentations 496 on the nozzle 460.

Referring collectively to FIGS. 10, 11A, 13, and 14B, during intended usage of the device 400, a user allows the nozzle to return to the completely extended position following each application of the medicine, and after an application is completed, the nozzle 460 locks in the completely extended position by engaging the lower indentation with dose lock 420. A user may, however, inadvertently, or intentionally partially depress the nozzle at the same time that a dose lock 420 (see FIGS. 13 and 14B) of the housing 402 is engaged. In this case, the upper indentation is positioned to engage the dose lock 420 and inhibit the nozzle from further depression when the nozzle is partially depressed. At least the upper indentation can have an angled shape such that although the nozzle 460 is inhibited from further depression, the vial lock can slide downward out of the indentation 496 to allow the nozzle 460 to extend further from the housing 402. In usage, if the upper indentation is engaged by the vial lock at the time that the nozzle 460 is locked, when depression force is removed from the nozzle 460, the spring 478 pushes the nozzle 460 out of the housing 402 toward the completely extended position. The dose lock 420 can thereby slide from the upper indentation to the lower indentation. Although one upper indentation is shown, the housing 402 can further include additional angled indentations positioned to engage the vial lock when the nozzle 460 is depressed at multiple partial depression positions. The angled notches can thereby function as a ratchet, allowing one way movement of the nozzle 460 when the vial lock is engaged. Number and position of the angled notches can be determined by physical design constraints as understood by a person skilled in the pertinent art.

Ratcheting action of the dose lock 420 can thereby lock out a user who attempts to subvert the dose lock 420 when the user applies a dosage (by depressing the nozzle 460), then slowly releases the nozzle 460 toward the extended position, stopping just short of reaching the completely extended position and engaging the lower indentation 496 (see also FIG. 13), and then attempts to again depress the nozzle 460.

Referring to FIG. 11B, the housing interface 480 can further include a vial lock opening 498. The vial lock opening 498 can be shaped, sized, and otherwise configured to engage a vial lock 430 (see FIGS. 13 and 14B) of the housing 402. When the vial lock is extended into the opening 498, the engagement of the vial lock to a lower ledge 499 of the opening 498 can inhibit the nozzle from being pulled out of the housing 402. The opening 498 can be sized so that the vial lock travels freely through the opening 498 when the nozzle 460 is depressed to deliver medication. The opening can further be sized such that the vial lock engages an upper ledge 497 of the opening 498 to set the completely extended position of the nozzle 460. Alternatively, the completely extended position of the nozzle 460 can be set and/or aided through engagement of additional features on the housing 402 and housing interface 480 as understood by a person skilled in the pertinent art according to the teachings of the present disclosure.

Figure 15:
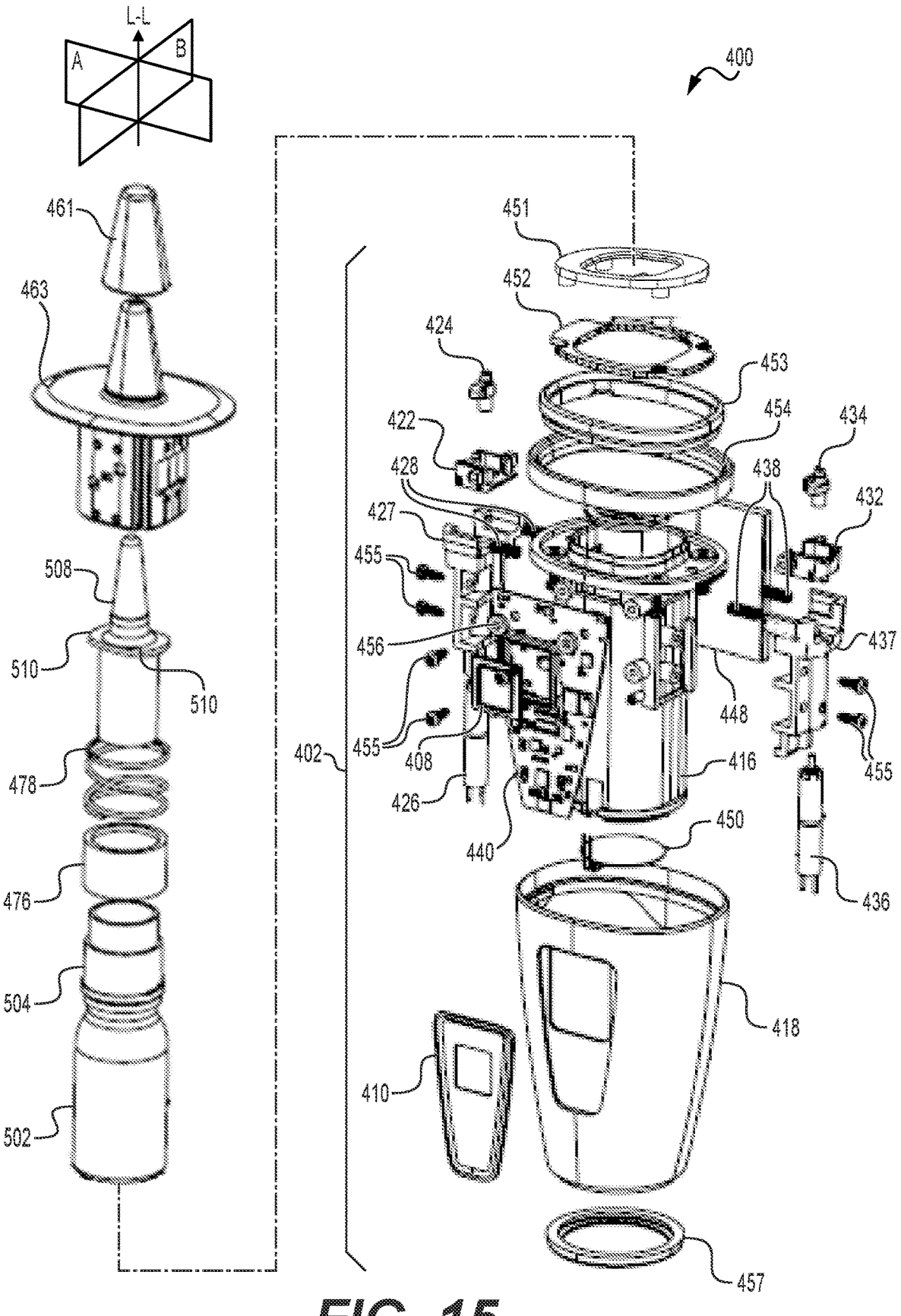
FIG. 15 is an exploded view of the dispensing device illustrated in FIG. 9 according to the present invention.

FIG. 13 is a cross sectional view of the device 400 oriented as illustrated in FIG. 9 and cut along plane B. Several of the components of the housing 402 are removed to highlight the dose lock 420 and vial lock 430. Additional components of the housing 402 (including a chassis 416) are illustrated in FIGS. 14B and 15.

Each of the locks 420, 430 respectively includes a motor 426, 436, a cam 424, 434, and a sliding extension 422, 432. When the nozzle 460 is at the completely extended position as illustrated, the sliding extension 422 of the dose lock is engaged to the lower indentation 496 on the housing interface 480 and the sliding extension 432 of the vial lock is engaged to the lower ledge 499 of the vial lock opening 498 of the housing interface 480.

When the dose lock 420 and vial lock 430 are both locked and the nozzle is in the completely extended position, the dose lock 420 prevents depression of the nozzle 460 and the vial lock prevents extension of the nozzle 460. When the dose lock 420 is open, the vial lock 430 provides a stop to set the completely depressed position of the nozzle 460.

The lower ledge 499 of the vial lock opening 498 and a bottom, mating surface of the sliding extension 432 of the vial lock 430 are each angled downward and inward. When in this position, the vial lock 430 is inhibited from disengaging the housing interface 480 while the dose lock 420 remains engaged to the lower indentation 496. If a user were to attempt to pull the nozzle 460 out of the housing 402, the sliding extension 432 can slide against the lower ledge 499, extending further into the housing interface 480, thereby further engaging the housing interface 480.

To remove the nozzle 460 and vial 500, an authorized user (e.g. physician or pharmacist) will send a command to the dispensing device 400 to remove the vial 500. The dose lock 420 will disengage, the authorized user will push the nozzle 460 down to disengage the undercut on the housing interface 480, a sensor (e.g. optical sensor viewing one or more openings 490, 492, 494) will sense the nozzle 460 is depressed, and the vial lock 430 will unlock and the vial 500 can then be removed.

Opening of each lock 420, 430 can include rotation of the respective motor 426, 436 which causes the respective cam 242, 434 to turn and the respective sliding extension 422, 432 to slide outwardly, away from the housing interface 480, thereby disengaging the housing interface 480. Closing of each lock 420, 430 can include reverse rotation of the respective motor 426, 436 which causes the respective cam 242, 434 to turn opposite from opening to release the respective sliding extension 422, 432, allowing springs 428, 438 (FIG. 14B) to push the respective sliding extension 422, 432 toward the housing interface 480, thereby engaging the housing interface 480.

The dose lock 420 can include an angled sliding extension 422 shaped to engage indentations 496 on the housing interface 480 of the nozzle 460. The extension 422 of the dose lock 420 can ratchet across multiple indentations 496 (see FIG. 11A).

FIGS. 14A and 14B are each a top down view of the housing 402, orthogonal to planes A and B. FIG. 14B is a cross-sectional view of the housing 402 cut at plane C as indicated in FIG. 13.

FIG. 14A illustrates the top surface 404*a*, opening 412, chamber cavity 414, sliding extension 422 of the dose lock 420, and sliding extension 432 of the vial lock 430. The vial lock 430 includes an upper and lower fin. The lower fin is shaped to engage the lower ledge 499 of the vial lock opening 490 of the housing interface 480 of the nozzle 460 as illustrated in FIG. 13. The upper fin is shaped to engage the upper ledge 497 of the vial lock opening 498 to set the completely extended position of the nozzle 460. The opening 412 includes a key extension 413. The housing interface 480 is indented on the side illustrated in FIG. 10 for proper orientation of the nozzle 460 when the housing interface 480 is inserted into the opening 412.

FIG. 14B illustrates additional component parts of the housing 402 and locks 420, 430. Each lock 420, 430 includes respective springs 428, 438 attached to the respective sliding extensions 422, 432 to move the locks 420, 430 to the closed position when the respective cams are positioned as illustrated. The cams 424, 434 are positioned as mirror images of each other, and can alternatively be otherwise positioned as understood by a person skilled in the pertinent art according to the teachings of the present disclosure. To open the locks 420, 430 the cam 424 of the dose lock 420 rotates clockwise and the cam 434 of the vial lock 430 rotates counterclockwise (i.e., in opposite directions due to mirror symmetry of cams 424, 434). As the respective cams 424, 434 rotate, they engage a respective bump 423, 433 on the respective sliding extension 422, 432, thereby pushing against the springs 428, 438 and moving the sliding extension 422, 432 outwardly to the open position. The bumps 423, 433 are centered on the respective sliding extension 422, 432 to minimize sideways movement of the extension 422, 432, thus reducing the risk of jamming the lock compared to a non-centered engagement. The bumps 423, 433 and cams 424, 434 are preferably configured such that the cams 424, 434 have a small contact area and therefore lower friction compared to a larger contact area.

Another option is to have one or both cams 424, 434 rotate past 90 degrees over the bump 423, 433. This option does not rely on the friction of a motor gearbox to keep the lock open 420, 430 and thus allows for more options on motor selection.

Each lock 420, 430 includes stops 415, 417 against which a vertical extension 425, 435 of the respective cam 424, 434 presses when the cam has reached the end of its rotational travel. Each stop 415, 417 is preferably integral to a chassis 416 (see also FIG. 15) of the housing 402, rather than to the respective sliding extension 422, 432. Stops 415, 417 integral to the chassis 416 can reduce likelihood of rotation (and therefore jamming) of the respective sliding extension 422, 432 when the respective cam 424, 434 engages the respective stop 415, 417 compared to stops integral to the sliding extensions 422, 432. The chassis 416 can also provide structural support for, or otherwise be engaged to the springs 428, 438 and motors 426, 436.

Referring still to FIG. 14B, the housing 402 includes a printed circuit board 440 with electrical components connected thereto that together form electrical circuitry for performing various functions of the device 400. The circuit board 440 can include a processor and non-transitory computer readable medium with instructions thereon that when executed by the processor cause the electrical circuitry to perform functions described herein, including functionality described in relation to the system illustrated in FIG. 1. The circuit board 440 need not have the specific form as illustrated. The electrical circuitry of the housing 402 can include a ridged board, a flexible circuit, discrete components, free wiring, and/or combinations thereof, for instance. Several forms of electrical circuitry can be utilized to carry out the functions described herein as understood by a person skilled in the pertinent art according to the teachings of the present disclosure. The electrical circuitry of the device 400 can further include a medication sensor 138, tactile switch 140, and/or real-time clock as described elsewhere herein.

The electrical circuitry includes three optical sensors 442, 444, 446 mounted to the circuit board 440. Each sensor 442, 444, 446 is positioned to view a respective opening 494, 492, 490 in the housing interface 480 of the nozzle 460. Each sensor 442, 444, 446 is configured to provide a sensor signal indicative of a depressed position of the housing interface. At least the middle sensor 444 is positioned to provide a sensor signal indicative of a partially depressed position of the nozzle between the completely extended position and the completely depressed position. Monitoring partial depression of the nozzle 460 can be useful to determining proper administration of the medication and/or for tamper prevention. In some embodiments, the electrical circuitry can be configured to close the dose lock 420 in response to receiving a sensor signal from the middle sensor indicative of a prolonged partially depressed position and/or a repeated partial depression of the nozzle 460. In some embodiments, the processor is configured to receive the sensor signal and execute instructions in the memory to cause the electrical circuitry to activate the motor 426, thereby turning the cam 424 and closing the lock 420.

The device 400 can include additional or alternative sensors and/or indicators for detecting partial depression of the nozzle 460. As one example, the housing interface 480 can include a high contrast image in place of the openings such as a series of horizonal lines across the outer surface 482 of the housing interface 480. As the nozzle 460 is depressed, the electrical circuitry can determine the number of lines which have passed in front of one or more optical sensors 442, 444, 446 based on signals from the sensor(s). Additionally, or alternatively, the horizontal lines can vary in thickness, to thereby create a distinct sensor signal depending on which line is viewed by the optical sensor. As another example, the housing interface 480 can include a conductive strip, and circuit board 440 can include two or more contacts positioned to simultaneously come into electrical contact with the conductive strip when the nozzle 460 is partially depressed. Electrical circuitry of the housing 402 can detect when the contacts are shorted to thereby detect partial depression of the nozzle 460 at one or more partial depression positions.

The top and bottom openings 490, 494 can be used to determine when the nozzle 460 is in the completely extended positioned or completely depressed position. Alternatively, the housing 402 can include limit switches to detect when the nozzle 460 is in the completely extended and/or completely depressed position.

Engagement of the cam 424, 434 to the stops 415, 417 can be detected by monitoring current to the respective motor 426, 436. When the electrical circuitry detects an increase in current over a predetermined threshold (e.g. as provided by the instructions in the memory), the electrical circuitry can reduce or remove power to the motor 426, 436.

The electrical circuitry can further include a sensor (e.g. optical sensor) for detection of a vial 500.

The electrical circuitry can be powered by a battery 448 integrated into the housing 402. The electrical circuitry can include battery charging regulation and battery protection circuitry (e.g. over-voltage, under-voltage, over-current, etc.).

The electrical circuitry can be configured to hold the dose lock 420 for the set amount of doses (e.g. as entered by a physician or pharmacist), then returns the dose lock 420 to closed/lock position. When returned to closed/lock position the springs 428 push the dose lock extension 422 to engage the housing interface 480.

FIG. 15 is an illustration of an exploded view of component parts of the device 400 and vial 500. The nozzle 460 includes the handle portion 463, spring 478, and retention ring 476. The vial 500 includes a liquid container 502, an atomizer 504, and a vial nozzle 508. The housing 402 includes a top cover 451, a light guide 453, and a top ring 454 which together form the top surface 404a of the housing 402. The housing 402 further includes a light emitting diode (LED) board 452 including LEDs positioned to illuminate the light guide 453. The same or additional LEDs can provide illumination for optical sensors in the housing 402. Components parts of the dose lock 420 and vial lock 430 are secured to the chassis 416 by a respective lock cover 427, 437. The circuit board 440 includes a scan nest 456 mounted thereon to which the biometric sensor 408 can be mounted.

The lock covers 427, 437 and circuit board 440 are affixed to the chassis by screws 455. Of course, alternative fasteners, glues, snaps, or other strategies can be used to secure component parts to the chassis 416 and/or within the housing 402 as understood by a person skilled in the pertinent art according to the teachings of the present disclosure.

The housing 402 can be charged via inductive charging. The housing 402 includes an inductive coil 450 positioned near the bottom end 406 of the device 400, inside of the cover 418. The cover 418 can include a co-mold ring 457 near the bottom end 406 for added stability to inhibit the device 400 from overturning during charging. Electronic circuitry of the housing 402 can include circuitry for inductively charging the battery 448 with the coil 450 including circuitry designed according to currently available inductive chargers and other such wireless charging schemes yet to be developed. Incorporating wireless charging into the housing eliminates the need for a charging port, which eliminates a point of ingress for the user and therefore can provide a device that is more robust against tampering compared to a device with a wired charging port. Further, because the user does not have direct access to the charging mechanism, a device with wireless charging can be more resistant to damage (at least to the charging circuit) compared to a device with a wired charging port.

The entire assembly has no screws exposed with the cover 418 clipping over the chassis 416. The function of parts, mechanical and electrical, can be assembled and tested on the chassis 416 before the cover 418 is clipped over.

Figures 16A, 16B, 16C:
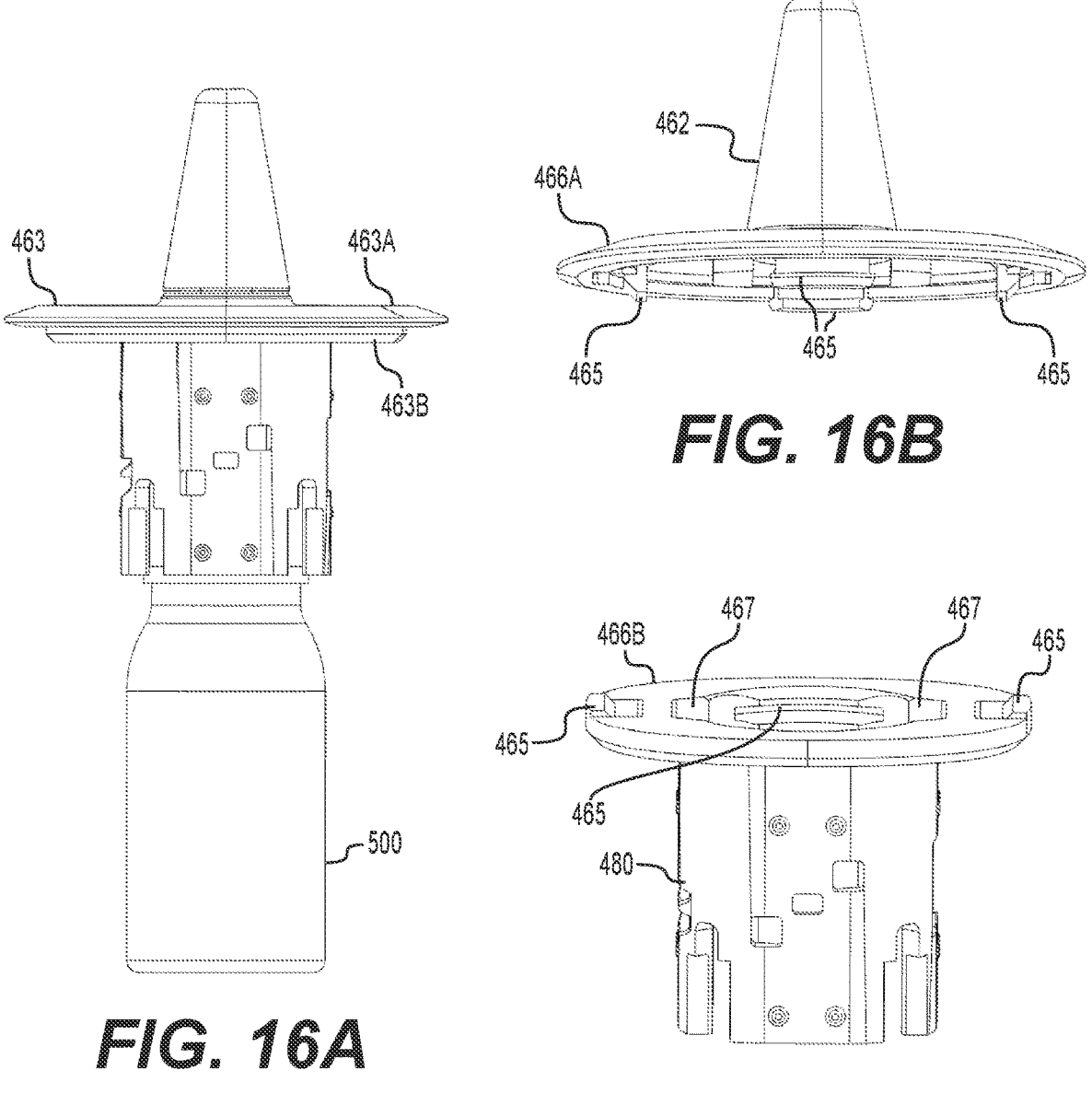
FIGS. 16A through 16C are illustrations of an alternative handle portion of a nozzle of the dispensing device illustrated in FIG. 9 according to the present invention.

FIGS. 16A through 16C are illustrations of an alternative handle portion 463 of a nozzle of the dispensing device 400 illustrated in FIGS. 11A and 11B. The handle portion 463 includes an upper portion 463a and a lower portion 463b that are manufactured as two separate parts. The upper portion 463a and 463b include clips 465 that can engage each other to secure the upper portion 463a to the lower portion 463b in a tamper resistant way, meaning the upper portion 463a and lower portion 463b are not easily separable by a recipient of the medication. The handle portion 463 can include a cradle 467 sized to house depression tabs 510 of a vial nozzle 508 (see FIG. 15). The cradle 467 can be sized to house larger depression tabs 510 that may be found on many medicinal vials 500 presently used in the industry.

The nozzle 460 of the dispensing device 400 having a handle portion 463 as illustrated in FIGS. 16A through 16C can be fitted to the vial 500 by removing the vial nozzle 508 from the vial 500, placing the retention ring 476 and spring 478 over the vial 500, sliding the housing interface 480 over the spring and retention ring 476, placing the vial nozzle 508 onto the vial 500 such that the depression tabs 510 are positioned within the cradle 467 of the lower portion 463b of the handle portion 463, and snapping the upper portion 463a of the handle portion 463 over the vial nozzle 508 and secured the lower portion 463b of the handle portion 463. The sequence of affixing the nozzle 460 to the vial 500 can be carried out in a variety of ways, with steps performed in different order than listed as understood by a person skilled in the pertinent art; for instance, the vial nozzle 408, spring, and/or retention ring 476 can be secured within the handle portion 463 before the vial 500 is inserted into the handle portion 463. The housing interface 480 can include flexible hooks 481 that extend to move over the vial 500 and snap under a ridge on the vial to engage and secure the nozzle 460 to the vial 500. Once the nozzle 460 of the dispensing device is attached to the vial 500, the nozzle 460 can be inserted into the housing 402 and the dispensing device 400 can function as described in relation to FIGS. 9 through 15.

FIGS. 16A through 16C illustrate one example geometry of a handle portion 463 having separate portions that can secure a vial nozzle 508 in a tamper proof fashion. Other alternatives including a handle portion 463 including two vertically divided portions and/or more than two separate portions can be constructed as understood by a person skilled in the pertinent art.

FIG. 17 is an illustration of an exploded view of another embodiment of the dispensing device 600 according to the present invention. FIG. 18A is an illustration of a cross-sectional view of the dispensing device in plane A as indicated in FIG. 17. FIG. 18B is an illustration of a cross-sectional view of the dispensing device in plane B as indicated in FIG. 17.

Distinctions between the dispensing device 600 illustrated in FIG. 17 and the device 400 illustrated in FIGS. 9 through 15 include the vial 500 being loadable from the bottom of the device 600 and the nozzle being integral with (i.e. non-separable from without damaging or specialized disassembly) the housing. The dispensing device 600 illustrated in FIG. 17 can have electrical circuitry and components (e.g. mechanical and/or electrical components) to perform partial dosage detection, biometric scanning, wireless and/or wired communication to other computing devices, programmability for timed dosage, micro-movement detection, drug identification, medication quantity sensing, and other such functionality as described in relation to other dispensing device embodiments 100, 400 described elsewhere herein.

Referring collectively to FIGS. 17, 18A, and 18B, the dispensing device 600 includes a handle portion 663, top cover 651, LED board 652, light guide 653, top rim 654, housing interface 680, spring 678, chassis 616, battery 648, biometric sensor 608, sliding dose lock extension 622, dose lock cam 624, dose lock motor 626, c-shaped vial lock extension 632, vial lock cam 634, vial lock motor 636, circuit board 640, cover 618, finger cover 610, cover co-mold 657, and base 658.

The top cover 651, LED board 652, light guide 653, and top rim 654 assemble similar to the corresponding components 451, 452, 453, 454 of the dispensing device 400 illustrated in FIGS. 9 through 15.

The nozzle of the device 600 includes the handle portion 663, spring 678, and housing interface 680. The handle portion 663 includes a conical portion and engagement ring similar to the conical portion 462 and engagement ring 466 of the handle portion 463 of the nozzle 460 of the dispensing device 400 illustrated in FIGS. 9 through 15. The handle portion 663 and housing interface 680 clip to each other.

The housing interface 680 has an outer surface 682 which includes features thereon for detection of partial depression of the nozzle similar to features on the outer surface 482 of the housing interface 480 of the dispensing device 400 illustrated in FIGS. 9 through 15. Likewise, the electrical circuitry (i.e. circuit board 640 and other electrical components) of the device 600 include sensors for detecting position and/or movement of the features on the housing interface 680.

The device 600 includes limit switches to detect when the nozzle of the device 600 is in the completely extended and/or completely depressed position. Additionally, or alternatively, the device 600 can include openings in the housing interface 480 similar to openings 490, 494 of the device 400 illustrated in FIG. 10 to detect when the nozzle of the device 600 is in the completely extended and/or completely depressed position.

The housing interface 680 further includes indentations 696 positioned to engage the dose lock extension 622. The indentations 696 can be angled to inhibit depression and allow extension of the nozzle when the handle 663 is partially depressed. The dose lock 620 (including dose lock extension 622, cam 624, and motor 626) can ratchet across the indentations 696 similar to the functionality of the dose lock 420 and indentations 496 of the device 400 illustrated in FIGS. 9 through 15. The dose lock extension 622 includes an angled ledge 695 that fits within the angled indentations 696. The dose lock extension 622 has a ring shape. The dose lock is pressed into the locked position by a spring 628. The cam 624 and motor 626 of the dose lock are positioned on an opposite side (compared to the angled ledge 695) of the ring of the dose lock extension 622. To open the dose lock, the motor 626 activates to turn the cam 624 which presses against the dose lock extension 622, against the force of the spring 628 to move the angled ledge 695 out of the indentations 696.

The vial lock 630 includes the c-shaped vial lock extension 632, vial lock cam 634, and vial lock motor 636. The general orientation of the vial lock 630 is upside down in comparison to the vial lock 430 of the device 400 illustrated in FIGS. 9 through 15 to facilitate removal of the vial 500 via the bottom 606 of the device 600. The base 658 fits into the chassis 616 and is held in place by engagement of the vial lock extension 632 to an indentation 698 on the base 658. To open the vial lock 630, the motor 636 is activated to rotate the cam 634, where thereby disengages the vial lock extension 632 from the indentation 698 on the base 658. The vial lock extension 632 is held in the locked position by a spring and is opened by activating the vial lock motor 636 to rotate the cam 634 to push the vial lock extension 632 against the spring. The base 658 can include multiple angled indentations to ratchet the base 658 into the device 600. The ratchet can inhibit movement of the base 658 out of the device 600 and allow movement of the base 658 into the device 600.

The vial lock 630 can alternatively include a ring gear lock that goes around the vial 500. The alternative design can increase system reliability and/or reduce production cost. A motor turns the ring gear lock thereby disengaging the vial lock while the vial holder/base 658 is in place. Once the vial 500 is not present the ring gear lock returns to the locked position. The base 658 can then be pushed back in to lock in place. Lock clips rely on the spring action of the plastic to move for the base to lock.

Position of the dose lock 620 and vial lock 630 are detected by measuring an increase in current when the respective cam 624, 634 is turned by the respective motor 626, 636 into a stop similar to as described in relation to the device 400 illustrated in FIGS. 9 through 15.

The device 600 further includes a sensor (e.g. limit switch or optical sensor) to detect presence of a vial 500.

The entire assembly can have no screws exposed with the cover 618 clipping over the chassis 616. Functionality of mechanical and electrical parts can be assembled and tested on the chassis 616 before the cover 618 is clipped over.

The device 600 includes a Mini USB port for charging. Alternatively, the device 600 can include a coil or inductive charging and/or an alternative charging port such as USB C, proprietary charging port, or other charging port as understood by a person skilled in the pertinent art according to the teachings of the present disclosure.

Figure 19:
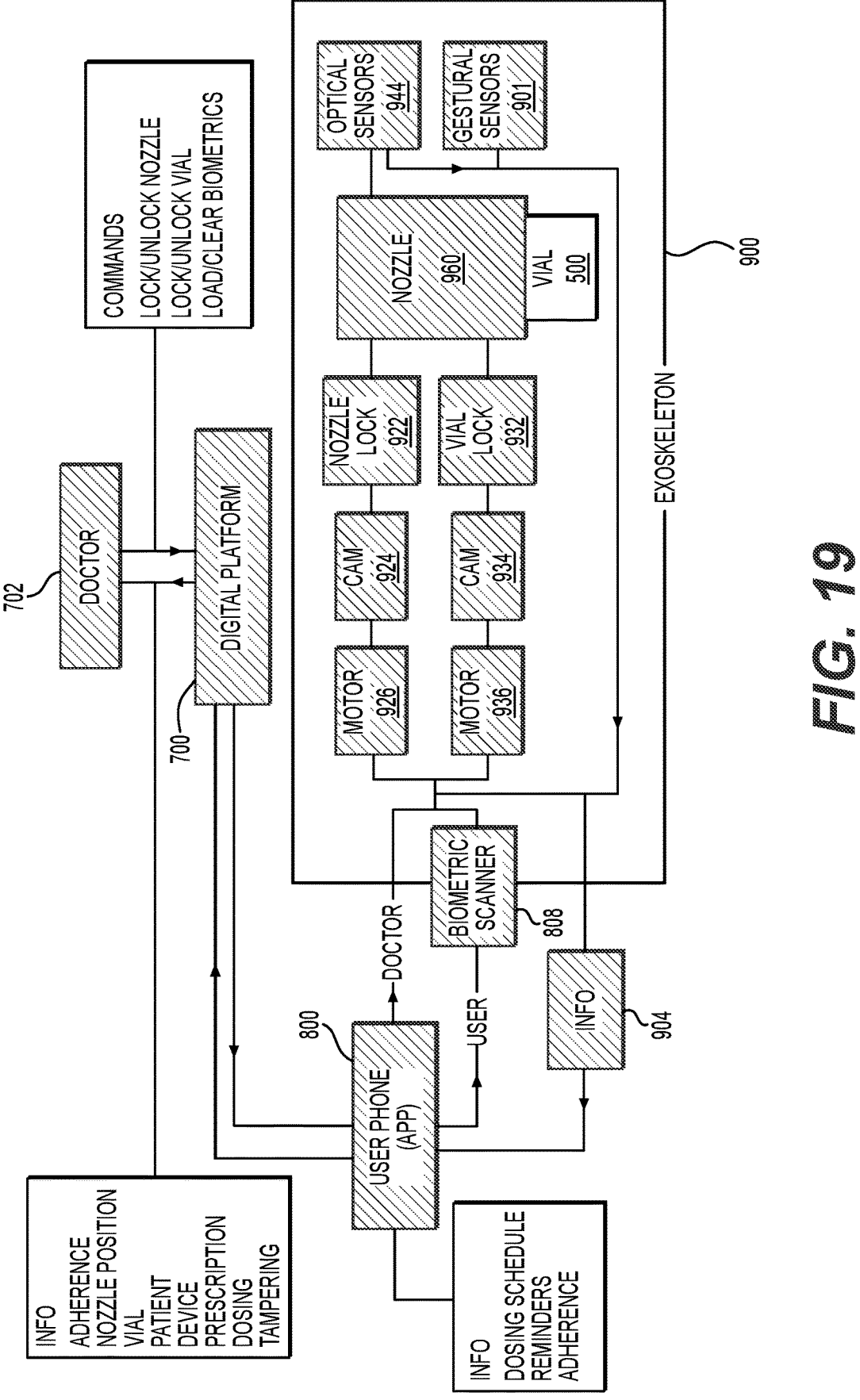
FIG. 19 is a block diagram of a system according to the present invention.

FIG. 19 illustrates a system diagram of an example system including a digital platform 700, a user device 800, and a dispensing device 900. The digital platform 700 and user device 800 can each include the computing device 200 illustrated herein, an alternative thereto, and/or a variation thereof as appreciated and understood by a person a person skilled in the pertinent art according to the teachings of the present disclosure. The dispensing device 900 can include any one of the dispensing devices 100, 400, 600 illustrated herein, an alternative thereto, and/or a variation thereof as appreciated and understood by a person skilled in the pertinent art according to the teachings of the present disclosure.

An authorized user 702 (e.g. doctor) can receive information related to prescription adherence, nozzle position, vial type, patient information, device information, prescription information, dosage information, and dispensing device tampering via the digital platform 700. The information can be provided as an output 904 of the dispensing device 900. The authorized user 702 can input commands related to nozzle locking/unlocking, vial locking/unlocking, and/or biometrics loading/clearing via the digital platform 700. The digital platform can communicate via an application on the user device 800 to the dispensing device 900.

A user (e.g. patient) can be authenticated by the dispensing device 900 via the user device 800 and/or biometric scanner 908. The user device 800 can further receive information related to dosing schedule, reminders, and prescription adherence from the dispensing device 900.

The dispensing device 900 can include a motor 926 and cam 924 positioned to engage a nozzle locking mechanism 922. The motor 926, cam, 924, and nozzle locking mechanism 922 can have structure and/or functionality similar to structures of dispensing devices 100, 400, 600 described herein for locking nozzle position to prevent dosing, a variation thereof, or alternative thereto as understood by a person skilled in the pertinent art according to the teachings of the present disclosure.

The dispensing device 900 can include a motor 936 and cam 934 positioned to engage a vial locking mechanism 932. The motor 936, cam, 934, and vial locking mechanism 932 can have structure and/or functionality similar to structures of dispensing devices 100, 400, 600 described herein for securing a vial within a dispensing device, a variation thereof, or alternative thereto as understood by a person skilled in the pertinent art according to the teachings of the present disclosure.

The dispensing device 900 can house a vial such as vial 500 a variation thereof, or alternative thereto as understood by a person skilled in the pertinent art according to the teachings of the present disclosure.

The dispensing device 900 can include a nozzle 960 that can be depressed to dispense medication and provide features thereon for locking and/or dose detection as described elsewhere herein, variations thereof, and alternatives thereto as understood by a person skilled in the pertinent art according to the teachings of the present disclosure.

The dispensing device 900 can include optical sensors 944 for detecting partial depression of the nozzle 960, detecting presence of the vial 500, detecting ingress into the dispensing device 900 and/or other functionality of optical sensors as described elsewhere herein, variations thereof, and alternatives thereto as understood by a person skilled in the pertinent art according to the teachings of the present disclosure.

The dispensing device 900 can include gestural sensors 901 (e.g. micro movement sensors) to detect user specific movement patterns to detect when a different user handles the device 900.

Figure 20A:
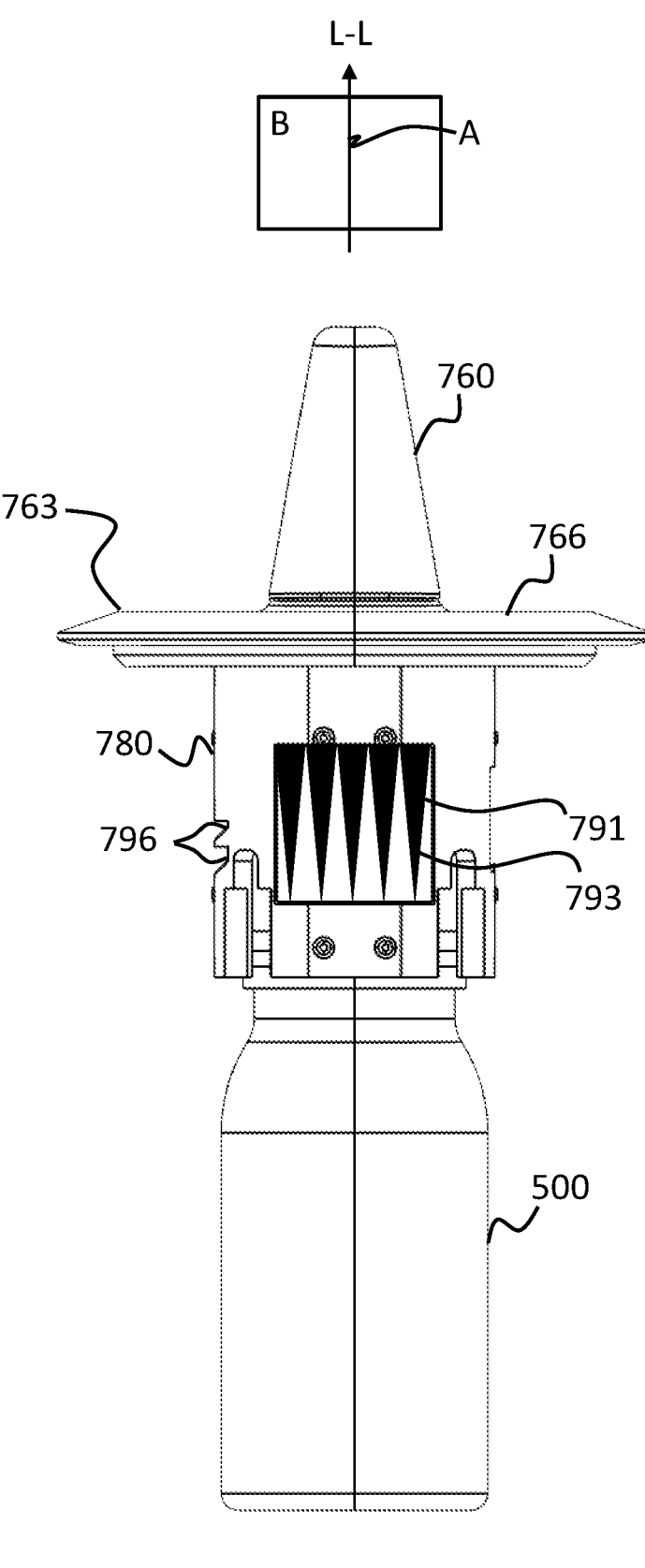
FIG. 20A is a side view of an alternative handle portion and vial according to the present invention.
Figures 20B, 21:
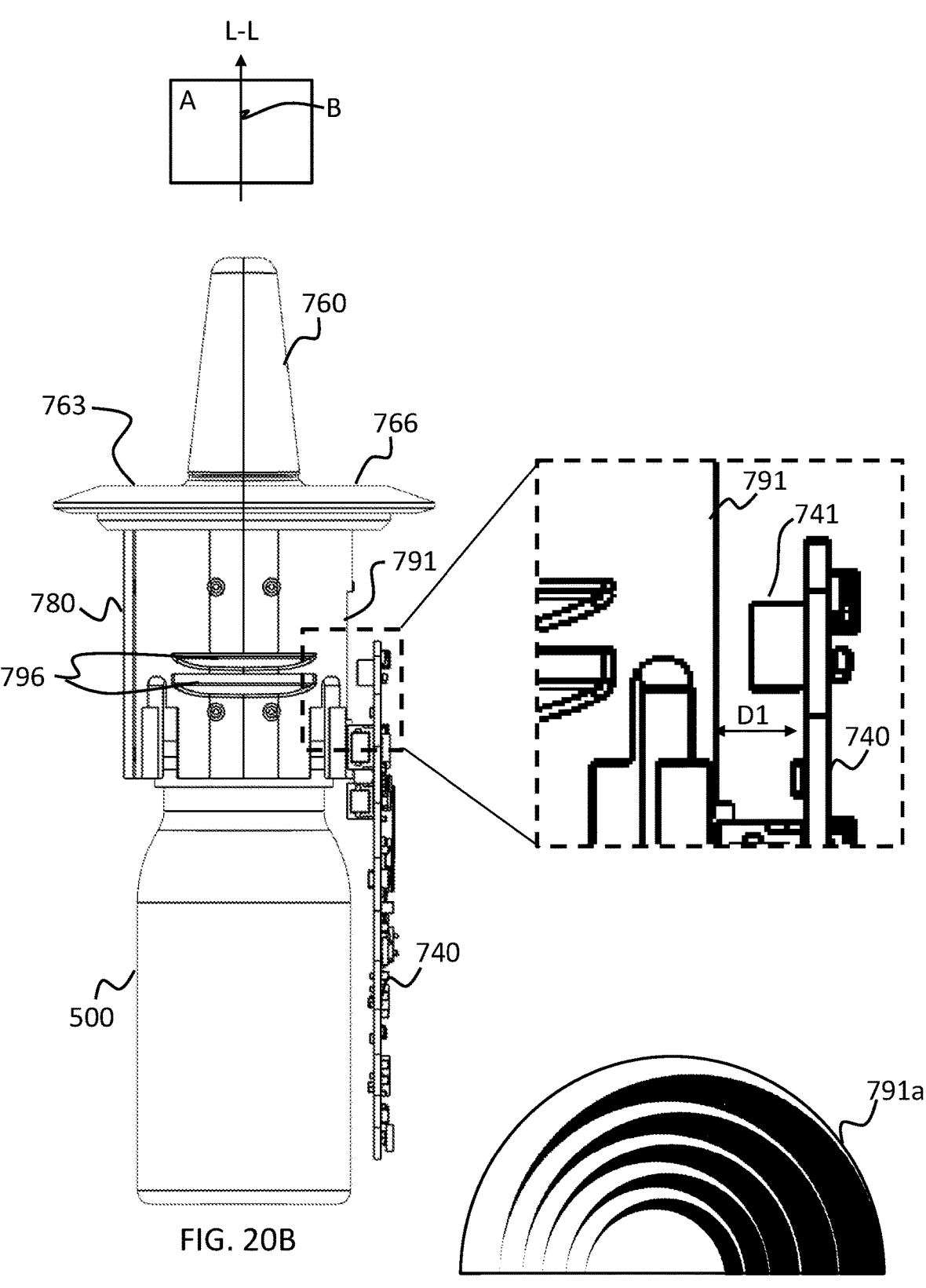
FIG. 20B is an orthogonal side view of the handle portion and vial in FIG. 20A with alternative circuit board according to the present invention.
FIG. 21 is an illustration of an image configured to provide reflectivity to a rotational sensor according to the present invention.

FIGS. 20A and 20B are illustrations of an alternative handle portion 763 and circuit board 740 that can be used in place of the handle portion 463 and circuit board 440 of the dispensing device 400 illustrated in FIGS. 9 through 16C. The handle portion 763 illustrated in FIGS. 20A and 20B can include a nozzle 760, engagement ring 766, and housing interface 780 with indentations 796 configured similarly to corresponding features 460, 466, 480, 496 of the handle portion 463 illustrated in FIGS. 9 through 16C. The handle portion 763 and circuit board 740 can be adapted to function with other dispensing devices disclosed herein, variations thereof, and alternatives thereto as understood by a person skilled in the pertinent art.

The handle portion 763 illustrated in FIGS. 20A and 20B includes a high contrast graphical image 791 in place of openings 490, 492, 494 illustrated in FIGS. 10, 15, 16A, and 16C. The circuit board 740 illustrated in FIG. 20B includes a sensor 741 positioned to view the high contrast graphical image 791 and associated hardware and software to operate the sensor 741. When the handle portion 763 is depressed or released, the image 791 moves with the handle portion 763.

The high contrast image 791 can be applied to the housing interface 780 by several means, for example, the image 791 can be printed onto a sticker that is then attached to the housing interface 780, the image 791 can be printed directly onto the housing interface 780, and/or the image 791 can be over-molded/co-molded with the housing interface 780 in a material that contrasts in visible light reflection and/or IR light reflection with a primary material of the housing interface 780. The image 791 can be sized about 14 millimeters (mm) by 14 mm. The image size can be adjusted to occupy a convenient portion of the housing interface 780, and/or the image size can be adjusted to achieve sensor resolution according to the teachings herein as understood by a person skilled in the pertinent art; for instance, the image may have a maximum size limit determined by area of housing interface 780 and other geometrical factors of the dispensing device 400 and a minimum size limit determined by a minimum sensor resolution design parameter. The image 791 can include dark triangles 793 on a light background or other such image that has a change in amount of dark space to light space in the direction of the longitudinal axis L-L. Bases of dark triangles can be aligned on a first end of the image 791 and bases of light triangles can be aligned on a second end of the image 791 such that the dark and light triangles are interleaved. As illustrated, the bases of the dark triangles are at the top of image 791 and the bases of the light triangles are at the bottom of the image 791; however, this orientation can be reversed with the bases of the light triangles at the top of the image 791 and the bases of the dark triangles at the bottom of the image 791 with modifications in software as understood by a person skilled in the pertinent art.

The sensor 741 can be configured to measure handle position in a single sample, without requiring comparison to a previous sample. The sensor 741 can be configured to determine length of depression of the nozzle 760 at a high degree of resolution. Resolution can be determined by several means as understood by a person skilled in the pertinent art. For the purposes of providing numerical values of resolution herein, output of the senor is recorded as the handle portion 763 is moved by a numerically controlled positioner over a range of about 5 mm. The recorded output is compared statistically against the controlled position to calculate repeatability and linearity of the sensor output. Linearity is expressed as the standard deviation of the differences in output from each position to the next when the handle portion 763 is moved in 0.5 mm increments over a range of 5 mm. Repeatability is expressed as the maximum of the standard deviations of the output samples for each position when the handle portion 763 is moved up and down five times over a range of 2 mm then over a range of 3 mm. Resolution, in counts per mm, is expressed as the number of sensor output counts between two positions 4 mm apart divided by 4, less the repeatability, and less the linearity.

In a preferred example, the sensor can have a resolution of at least about 4 counts per mm and up to more than 500 counts per mm. At about 815 counts per mm, the sensed depression can be accurate to about 64 counts or about 83 micrometers of measurement error. The sensor 741 can continuously operate at a sample rate of 10 samples per second, at an average power consumption of about 47 microwatts, with the resolution of about 815 counts per mm. In another example, the sensor can have a resolution of at least about 4 counts per mm and up to about 2350 counts per mm. At 2350 counts per mm, the sensed depression can be repeatable at about 20 counts or about 8 micrometers of measurement error. The sensor 741 can continuously operate at a current of 0.015 milliamperes (mA) at the resolution of 2350 counts per mm. The sensor 741 can continuously operate at a current of about 0.004 mA at a resolution of about 500 counts per mm.

The sensor 741 and image 791 can be low profile, preferably the main board of the circuit board 740 can be a distance D1 of about 2.5 millimeters from the housing interface 780. The sensor 741 can be separated from the housing interface 780 such that the graphical image 791 is not in contact with the sensor 741 so that depression of the housing interface 780 does not cause damage to the graphical image 791 nor the sensor 741. The sensor 741 can be immune to external fields and influences such as sunlight, magnets, etc. The sensor 741 can be robust against production tolerances and drift. The sensor 741 can be configured to have a high sample rate such that quick partial doses can be detected. The sensor 741 can be configured to detect vial presence. The sensor 741 and circuit board 740 can be configured to perform an automated calibration procedure when the handle portion 763 and vial 500 are inserted into the housing 402. The sensor 741 can include only a single sensor or can include a second sensor for calibration and/or redundancy. The sensor 741 can operate without lenses or other such optical features.

The sensor 741 can be configured to sense reflectivity of the image 791. The sensor 741 includes an infrared (IR) proximity sensor and preferably also includes a wide angle IR light emitting diode (LED). The IR LED can be positioned to illuminate the image 791. The sensor 741 can be configured to sense a change in IR reflectivity presented to the sensor 741 as the image 791 moves. The sensor 741 can be configured to detect presence of the vial 500 using IR distance sensing.

In general, IR proximity sensors are presently used in several applications such as auto focus, gesture recognition, etc. to detect motion or measure distance. When measuring distance, a beam of IR light is emitted and the IR proximity sensor measures intensity of IR light reflected from an object to a detector, where intensity is inversely proportional to distance from the object to the detector. To achieve good performance, these sensors utilize several techniques to cater for a large dynamic measurement range in the presence of strong interference (e.g. sunlight) and with very low power. An IR proximity sensor can include circuits, materials, and techniques, including those known in the art, to result in immunity to external fields and influences such as sunlight, magnets, etc.

IR proximity sensors are typically designed to sense targets positioned at a distance that is much greater than separation D1 between the sensor 741 and the image 791 as illustrated in FIG. 20B. As such, typical IR proximity sensors include a narrow beam IR emitter that is spaced away from the detector. The narrow beam is desirable to achieve accurate measurements at greater distances. The sensor 741 in the dispensing device 400 preferably includes a wide angle IR light source (e.g. LED) that is used in place of, or in addition to the narrow beam IR emitter. The narrow beam IR emitter may be used to determine presence of the vial 500, while the wide angle IR light source may be used to determine movement of the image 791, for example.

The image 791 preferably has a high contrast with respect to IR reflectivity. The image 791 can include black polyvinyl chloride (PVC) against white plastic and/or a black laser printed image on a white paper as non-limiting examples. A black thermally printed image on a white paper may have significantly less contrast with respect to IR reflectivity compared to the black polyvinyl chloride (PVC) against white plastic and/or a black laser printed image on a white paper.

Additionally, or alternatively, the sensor 741 can include a visible light sensor and a visible light source to detect depression of the handle portion 763. The visible light sensor can replace the IR proximity sensor for sensing depression of the handle portion 763 and/or be used in addition to the IR proximity sensor as a redundant and/or calibration sensor for depression of the handle portion 763.

The sensor 741 can be configured to perform a line scan of the image 791, and the line scan changes as the handle portion 763 moves. The sensor 741 can have a short dimension in the direction of the longitudinal axis L-L and a long dimension orthogonal to the longitudinal axis L-L, the long dimension being substantially greater than the short dimension.

FIG. 21 is an illustration of an image 791a configured to provide reflectivity to a rotational sensor. Principles described in relation to the sensor 741 and image 791 described in relation to FIGS. 20A and 20B can be used in other applications (i.e. not limited to the dispensing device 400) to provide a contactless, high-resolution sensor for determining position and/or angular rotation of component parts within a mechanical apparatus or system. The example image 791a can include tapered arcuate bands that have a wide base as a first angle of rotation and a tapered end at a second angle of rotation. Measuring angle counterclockwise, FIG. 21 illustrates tapered arcuate dark bands with wide bases at zero degrees and tapered ends at 180 degrees and interleaved tapered arcuate light bands with wide bases at 180 degrees and tapered ends at zero degrees. The image 791a can have shape geometrically related to a circle such as pie wedge, annulus, annulus sector, etc. The image 791 can have a center point defined by the trajectory of the tapered arcuate bands. The image 791a and sensor 741 can be secured in relation to each other at the center point of the image 791a. At least one of the sensor 741 and image 791a can be configured to rotate about the center point such that the sensor 741 moves to follow arcs of the arcuate bands and/or the image 791a moves to move the arcs of the arcuate bands across the sensor 741. Resolution of the sensor 741 can be determined in counts per unit angle (e.g. degree or radian).

Additional alternative means for sensing depression of the handle portion are also considered. Sensing means can be combined for redundancy and/or calibration in a dispensing device. A linear magnetic field sensor can be positioned to sense movement of a magnetic dipole on the handle portion such magnetic field strength and direction of magnetic field at the sensor changes as the handle portion moves. A capacitive sensor can include a metal plate on the circuit board and a metal plate on the handle portion such that an electric field is coupled between the sensor plates that has a magnitude proportionate to the overlap of the plates, and the overlap of the plates changes as the handle portion moves in relation to the circuit board. A resistive sensor can include a potentiometer positioned on the circuit board having knob that rotates against ribs on the handle portion when the handle portion moves relative to the circuit board, thereby changing resistance of the potentiometer. One or more microswitches can be positioned on the circuit board with rockers that engage mechanical ribs on the handle when the handle portion is moved relative to the circuit board to cause the microswitches to toggle between open and closed based on the depression of the handle portion. A photo-interruption sensor can include light sensor positioned to sense light through openings on the handle portion and a light source positioned to provide light through the openings in the handle portion; the openings can include horizonal ribs or a modulated scale. A magnetic field sensor can be positioned to sense a magnetic scale on the handle portion such that as the scale moves with the handle portion magnetic field at the sensor alternates. A motion tracking integrated circuit can be positioned to view an image on the handle such that as the handle moves in relation to the motion tracking integrated circuit, the motion tracking integrated circuit senses movement of the image. A color sensor can be positioned to view an image with a color gradient on the handle portion that is illuminated by a white light source such that as the image moves with the handle portion, color of light reflected to the color sensor changes. An image on the handle portion can have a black-white border and a sensor on the circuit board can include one or more of an IR photo-reflective sensor, an IR proximity sensor, and an ambient light sensor such that total amount of light reflected from the image to the sensor changes with position of the handle portion.

While the invention has been shown and described with reference to certain exemplary embodiments, it will be understood by one skilled in the art that various changes in detail may be made without departing from the spirit and scope of the invention, and without limiting the invention as claimed herein. Further, where exemplary embodiments are described with reference to a certain number of elements it will be understood that the exemplary embodiments can be practiced utilizing either less than or more than the certain number of elements.

What is claimed is:

1. A nasal spray device comprising:
   a nozzle comprising a conical nozzle portion extending along a longitudinal axis, a housing interface configured to attach to a vial, and a graphical image positioned on an exterior surface of the housing interface; and
   a housing comprising a chamber sized to receive the vial, an opening in communication with the chamber, and a sensor directed toward the graphical image, wherein a line of sight from the sensor to the graphical image is approximately tangential to the longitudinal axis,
      wherein the housing interface is positioned within the opening and configured to slide through the opening upon movement of the nozzle in relation to the housing, and
      wherein the sensor is configured to detect movement of the graphical image and determine a distance of depression of the nozzle upon movement of the nozzle along the longitudinal axis in relation to the housing.

2. The nasal spray device of claim 1, wherein the graphical image comprises a printed image upon a label affixed to the exterior surface of the housing interface.

3. The nasal spray device of claim 1, wherein the graphical image comprises a print directly applied to the exterior surface of the housing interface.

4. The nasal spray device of claim 1, wherein the graphical image comprises a distinct material composition from a majority of the housing interface and is over-molded and/or co-molded with the housing interface.

5. The nasal spray device of claim 1, wherein the graphical image comprises black and white features having a high contrast with respect to infrared light reflection.

6. The nasal spray device of claim 1, wherein the graphical image comprises interleaved black triangles and white triangles such that bases of the black triangles are aligned on a first end of the graphical image, bases of the white triangles are aligned on a second end of the graphical image, and heights of the white triangles and heights of the black triangles extend along the longitudinal axis.

7. The nasal spray device of claim 1, wherein the sensor is configured to measure a position of the nozzle in relation to the housing in a single sample, without requiring comparison to a previous sample.

8. The nasal spray device of claim 1, wherein the sensor is configured to measure position of the nozzle in relation to the housing with a measurement error of about 83 micrometers.

9. The nasal spray device of claim 1, wherein the sensor is configured with a measurement resolution of about 4 counts per millimeter (mm) to about 815 counts per mm.

10. The nasal spray device of claim 1, wherein the sensor is configured with a measurement resolution of about 500 counts per mm.

11. The nasal spray device of claim 10, wherein the sensor is configured to operate continuously at 10 samples per second at an average power of about 47 microwatts at the measurement resolution of about 500 counts per mm.

12. The nasal spray device of claim 1,
   wherein the housing further comprises a printed circuit board on which the sensor is affixed, and
   wherein a main board of the printed circuit board is positioned a distance of about 2.5 millimeters from the housing interface.

13. The nasal spray device of claim 1,
   wherein the sensor is further configured to detect presence of the vial in the chamber,
   wherein the sensor is further configured for automatic calibration in response to insertion of the vial into the chamber.

14. The nasal spray device of claim 1,
   wherein the sensor comprises an infrared (IR) proximity sensor configured to sense a change in IR reflectivity from the graphical image upon movement of the nozzle in relation to the housing, and
   wherein the sensor comprises a wide angle IR light emitting diode (LED).

15. The nasal spray device of claim 14, wherein the graphical image comprises laser printed ink on paper and/or polyvinyl chloride on plastic.

16. The nasal spray device of claim 14, wherein the IR proximity sensor is configured to sense presence of the vial in the chamber by distance sensing.

17. The nasal spray device of claim 1, wherein the sensor comprises a visible light sensor and a visible light source.

18. The nasal spray device of claim 1, wherein the sensor is configured to perform a line scan of the graphical image.

19. A nasal spray device comprising:

a nozzle comprising a conical nozzle portion extending along a longitudinal axis and a housing interface configured to attach to a vial, the housing interface comprising a graphical image positioned on an exterior surface, the exterior surface being substantially cylindrical and concentric with the longitudinal axis; and a housing comprising a chamber sized to receive the vial, an opening in communication with the chamber, and a sensor directed toward the graphical image and the longitudinal axis, wherein the housing interface is positioned within the opening and configured to slide through the opening upon movement of the nozzle along the longitudinal axis in relation to the housing, wherein the sensor is configured to detect movement of the graphical image positioned upon the exterior surface of the housing interface and determine a distance of depression of the nozzle upon movement of the nozzle along the longitudinal axis in relation to the housing.

\* \* \* \* \*